US012185886B2

(12) United States Patent
Madden et al.

(10) Patent No.: US 12,185,886 B2
(45) Date of Patent: Jan. 7, 2025

(54) SELF-CLEANING ENVIRONMENT

(71) Applicant: ALARM.COM INCORPORATED, Tysons, VA (US)

(72) Inventors: Donald Gerard Madden, Columbia, MD (US); Michael Kelly, Washington, DC (US); Matthew Daniel Correnti, Newtown Square, PA (US); Ethan Shayne, Herndon, VA (US); Robert Nathan Picardi, Herndon, VA (US)

(73) Assignee: Alarm.com Incorporated, Tysons, VA (US)

( * ) Notice: Subject to any disclaimer, the term of this patent is extended or adjusted under 35 U.S.C. 154(b) by 508 days.

(21) Appl. No.: 17/472,796

(22) Filed: Sep. 13, 2021

(65) Prior Publication Data
US 2022/0087498 A1 Mar. 24, 2022

Related U.S. Application Data

(60) Provisional application No. 63/082,765, filed on Sep. 24, 2020.

(51) Int. Cl.
A47L 11/40 (2006.01)
H04W 4/38 (2018.01)

(52) U.S. Cl.
CPC ......... A47L 11/4011 (2013.01); A47L 11/405 (2013.01); H04W 4/38 (2018.02); A47L 2201/06 (2013.01)

(58) Field of Classification Search
CPC ............ A47L 11/4011; A47L 11/405; A47L 2201/06; A47L 7/0085; A47L 9/2805; A47L 9/2836; A47L 9/2857; A47L 9/2884; A47L 9/2894; A47L 2201/00;
(Continued)

(56) References Cited

U.S. PATENT DOCUMENTS 4,595,419 A 6/1986 Patenaude
6,459,955 B1 10/2002 Bartsch et al.
8,963,623 B2 2/2015 Siao
(Continued)

OTHER PUBLICATIONS

Cairns, Rebecca, "What temperature kills germs? How to use heat properly to get rid of bacteria and viruses," Insider, Mar. 12, 2020, 14 pages.
(Continued)

Primary Examiner — Sze-Hon Kong
(74) Attorney, Agent, or Firm — Fish & Richardson P.C.

(57) ABSTRACT

Methods, systems, and apparatus, including computer programs encoded on computer storage media, for automatically cleaning a portion of an environment. One of the methods includes detecting, by an automated cleaning system, movement within a physical environment; determining, by the automated cleaning system and using data that represents the movement, that one or more threshold criteria for cleaning at least a portion of the physical environment are satisfied; and in response to determining that the one or more threshold criteria for cleaning at least the portion of the physical environment are satisfied, sending, by the automated cleaning system, an instruction to a device in the physical environment to cause the device to initiate a cleaning process of at least the portion of the physical environment.

20 Claims, 5 Drawing Sheets

(58) Field of Classification Search
CPC ........ A47L 2201/04; H04W 4/38; A61L 2/10; A61L 2202/17; A61L 2/24

See application file for complete search history.

(56) References Cited

U.S. PATENT DOCUMENTS

| | | | |
|---|---|---|---|
| 8,965,623 B2* | 2/2015 | Rakshit | G05D 1/0276 |
| | | | 700/250 |
| 10,463,217 B1 | 11/2019 | Bialek et al. | |
| 11,069,070 B2 | 7/2021 | Buibas et al. | |
| 11,274,929 B1* | 3/2022 | Afrouzi | G06T 7/62 |
| 11,398,309 B2 | 7/2022 | Correnti | |
| 11,416,878 B2* | 8/2022 | Koch | G06F 3/013 |
| 11,631,279 B2 | 4/2023 | Madden et al. | |
| 11,989,021 B1* | 5/2024 | Ebrahimi Afrouzi | |
| | | | G05D 1/0238 |
| 2006/0184293 A1 | 8/2006 | Konandreas et al. | |
| 2006/0190132 A1 | 8/2006 | Morse et al. | |
| 2006/0190133 A1 | 8/2006 | Konandreas et al. | |
| 2006/0190134 A1 | 8/2006 | Ziegler et al. | |
| 2006/0190146 A1 | 8/2006 | Morse et al. | |
| 2006/0200281 A1 | 9/2006 | Ziegler et al. | |
| 2007/0231189 A1 | 10/2007 | Jung et al. | |
| 2007/0231193 A1 | 10/2007 | Jung et al. | |
| 2007/0231204 A1 | 10/2007 | Hyde et al. | |
| 2009/0194137 A1* | 8/2009 | Friedman | A47L 9/281 |
| | | | 701/532 |
| 2010/0111775 A1 | 5/2010 | Hyde et al. | |
| 2010/0256812 A1 | 10/2010 | Tsusaka et al. | |
| 2011/0002821 A1 | 1/2011 | Hyde et al. | |
| 2011/0167574 A1 | 7/2011 | Stout et al. | |
| 2012/0213443 A1 | 8/2012 | Shin et al. | |
| 2012/0223216 A1 | 9/2012 | Flaherty et al. | |
| 2013/0206177 A1* | 8/2013 | Burlutskiy | G05D 1/0274 |
| | | | 15/319 |
| 2013/0270459 A1 | 10/2013 | Fontani | |
| 2014/0207280 A1 | 7/2014 | Duffley et al. | |
| 2014/0207281 A1* | 7/2014 | Angle | B25J 13/006 |
| | | | 700/257 |
| 2014/0207282 A1 | 7/2014 | Angle et al. | |
| 2014/0236351 A1 | 8/2014 | Hyde et al. | |
| 2014/0279458 A1 | 9/2014 | Holman et al. | |
| 2014/0324271 A1 | 10/2014 | Oh et al. | |
| 2014/0330452 A1 | 11/2014 | Stewart | |
| 2014/0358573 A1 | 12/2014 | Balinski et al. | |
| 2015/0166060 A1 | 6/2015 | Smith | |
| 2015/0197012 A1 | 7/2015 | Schnittman et al. | |
| 2015/0250372 A1 | 9/2015 | T P et al. | |
| 2016/0008982 A1* | 1/2016 | Artes | B25J 9/1664 |
| | | | 700/254 |
| 2016/0103451 A1 | 4/2016 | Vicenti | |
| 2016/0104084 A1 | 4/2016 | Philip et al. | |
| 2016/0274579 A1 | 9/2016 | So et al. | |
| 2017/0080570 A1 | 3/2017 | Schnittman et al. | |
| 2017/0197713 A1 | 7/2017 | Borman et al. | |
| 2018/0070787 A1 | 3/2018 | Gordon et al. | |
| 2018/0085927 A1 | 3/2018 | Kapoor et al. | |
| 2018/0125320 A1 | 5/2018 | Peck et al. | |
| 2018/0252534 A1* | 9/2018 | Kuhara | A47L 9/2857 |
| 2018/0296711 A1 | 10/2018 | Brais et al. | |
| 2018/0344116 A1 | 12/2018 | Schriesheim et al. | |
| 2019/0015984 A1 | 1/2019 | Kim et al. | |
| 2019/0025838 A1* | 1/2019 | Artes | G05D 1/0246 |
| 2019/0094869 A1* | 3/2019 | Artes | G05D 1/0044 |
| 2019/0102876 A1 | 4/2019 | Sanders et al. | |
| 2019/0117809 A1 | 4/2019 | Katz | |
| 2019/0176321 A1 | 6/2019 | Afrouzi et al. | |
| 2019/0191950 A1 | 6/2019 | Luo | |
| 2019/0212752 A1* | 7/2019 | Fong | G05D 1/0274 |
| 2019/0239709 A1 | 8/2019 | Thomas | |
| 2019/0343355 A1 | 11/2019 | Han et al. | |
| 2019/0357431 A1* | 11/2019 | Kamfors | A01D 34/008 |
| 2020/0100639 A1 | 4/2020 | Ullmann et al. | |
| 2020/0168339 A1* | 5/2020 | Correnti | G16H 40/67 |
| 2020/0268225 A1* | 8/2020 | Ashbaugh | A47L 11/185 |
| 2020/0306989 A1* | 10/2020 | Vogel | B25J 9/1653 |
| 2020/0380701 A1 | 12/2020 | Buibas et al. | |
| 2020/0394584 A1* | 12/2020 | Walsh | G06Q 10/063114 |
| 2021/0177226 A1 | 6/2021 | Burns et al. | |
| 2021/0235954 A1* | 8/2021 | Papenheim | G05D 1/0219 |
| 2021/0373558 A1* | 12/2021 | Schneider | G05D 1/0016 |
| 2022/0047141 A1* | 2/2022 | Xu | A47L 11/4055 |
| 2022/0269943 A1* | 8/2022 | Szatmary | G06N 5/04 |
| 2022/0359086 A1 | 11/2022 | Correnti | |
| 2023/0000302 A1* | 1/2023 | Oyaizu | G06T 7/0008 |
| 2023/0079349 A1* | 3/2023 | Jiang | A47L 9/0477 |
| | | | 134/18 |
| 2023/0168670 A1* | 6/2023 | von Reventlow | G05D 1/0231 |
| | | | 701/2 |

OTHER PUBLICATIONS

Emont, Jon, "Will Warmer Temperatures Bring a Coronavirus Reprieve? It's Complicated; Many scientists predict reduced spread in warm months, but can't say by how much," Wall Street Journal (online), Apr. 13, 2020, 3 pages.

PCT International Search Report and Written Opinion in International Appln. No. PCT/US2021/050028, dated Dec. 12, 2021, 7 pages.

* cited by examiner

SELF-CLEANING ENVIRONMENT

CROSS-REFERENCE TO RELATED APPLICATION

This application claims the benefit of U.S. Provisional Application No. 63/082,765, filed on Sep. 24, 2020, the contents of which are incorporated by reference herein.

BACKGROUND

Video cameras can capture a video sequence that includes one or more frames, e.g., images. A system can analyze the video sequence to determine content depicted in the video sequence. For instance, a system can analyze frames received from a camera to determine whether the frames depict people.

SUMMARY

A system uses analytics to initiate a cleaning process for a physical environment, a device within the physical environment, or both. When a person has accessed the physical environment, the system can monitor the person's movement through the physical environment and perform automated actions in response to the person's movement.

For instance, a smart device can detect when the person presses a button on the device and, upon determining that one or more criteria are satisfied, initiate a self-cleaning process. The self-cleaning process can include activating heating elements included in the smart device for a time period so that any pathogens on the smart device, e.g., because of the button press, are likely decontaminated. The criteria can require the self-cleaning process when the smart device will likely be used by another person within a threshold time period, will likely be used by an at risk person, or according to a schedule.

In some examples, the system can initiate a self-cleaning process for the physical environment once the person, and any other people who were in the physical environment, have left the physical environment. This can include the system providing instructions to smart devices to initiate a self-cleaning process; initiating a heating, ventilation, and air conditioning ("HVAC") process to raise a humidity level in the physical environment to reduce a likelihood of pathogens remaining in the air of the physical environment; exposing one or more parts of the physical environment to infrared or ultraviolet light; or a combination of these.

In some implementations, the system can receive video data of an environment, analyze the video data to detect areas that satisfy a threshold likelihood of needing cleaning, and guide the cleaning process of those areas. The cleaning process can be automated or manual, e.g., the system can provide instructions to a device to initiate a self-cleaning process.

The system can receive video data from a camera and analyze the video data to determine areas of the environment that have been used and satisfy a threshold likelihood of needing cleaning. The system can detect areas that have been used by anyone, by a person who is likely sick, or people or animals that satisfy other threshold criteria. The system can determine that a person is likely sick based on the person's interactions with the environment, e.g., whether the person sneezes, uses a tissue, etc. The system can determine the areas of the environment with which the person has likely interacted and determine that those areas satisfy the threshold likelihood of needing cleaning.

The system can use analytics to determine areas in the environment that have been cleaned, e.g., from the areas that satisfied the threshold likelihood of needing cleaning. The system can analyze video data of cleaning persons, sensor data from cleaning equipment, or both, to determine the areas that have been cleaned.

The system can use a difference between the areas that satisfy the threshold likelihood of needing cleaning and the areas that have been cleaned to determine areas that still likely need cleaning. The system can provide instructions for presentation of a user interface, or instructions to an automated device, that identifies these areas and indicates that these areas still need cleaning.

In general, one innovative aspect of the subject matter described in this specification can be embodied in methods that include the actions of detecting, by an automated cleaning system, movement within a physical environment; determining, by the automated cleaning system and using data that represents the movement, that one or more threshold criteria for cleaning at least a portion of the physical environment are satisfied; and in response to determining that the one or more threshold criteria for cleaning at least the portion of the physical environment are satisfied, sending, by the automated cleaning system, an instruction to a device in the physical environment to cause the device to initiate a cleaning process of at least the portion of the physical environment.

In general, one innovative aspect of the subject matter described in this specification can be embodied in methods that include the actions of detecting, by an automated cleaning system, movement within a physical environment; determining, by the automated cleaning system and using data that represents the movement, that one or more threshold criteria for cleaning at least a portion of the physical environment are not satisfied; and in response to determining that the one or more threshold criteria for cleaning at least the portion of the physical environment are not satisfied, determining, by the automated cleaning system, to skip sending an instruction to a device in the physical environment to cause the device to initiate a cleaning process of at least the portion of the physical environment.

In general, one innovative aspect of the subject matter described in this specification can be embodied in methods that include the actions of detecting, by an automated cleaning system, movement of a person within a physical environment; determining, by the automated cleaning system and using data that represents the movement of the person, that one or more threshold criteria for cleaning at least a portion of the physical environment are satisfied; detecting, by the automated cleaning system, one or more areas of the physical environment that have likely been cleaned sufficiently; determining, by the automated cleaning system, that the one or more areas of the physical environment that have likely been cleaned sufficiently do not include the portion of the physical environment for which the threshold criteria are satisfied; and in response to determining that the one or more areas of the physical environment that have been cleaned sufficiently do not include the portion of the physical environment for which the threshold criteria are satisfied, sending, by the automated cleaning system, an instruction to a device in the physical environment to cause the device to present a notification that identifies the portion of the physical environment that likely was insufficiently cleaned.

In general, one innovative aspect of the subject matter described in this specification can be embodied in methods that include the actions of detecting, by an automated cleaning system, movement of the person within a physical environment; determining, by the automated cleaning system and using data that represents the movement of the person, that one or more threshold criteria for cleaning at least a portion of the physical environment are satisfied; detecting, by the automated cleaning system, one or more areas of the physical environment with cleanliness levels that satisfy a threshold cleanliness level; determining, by the automated cleaning system and using data for the one or more areas of the physical environment with cleanliness levels that satisfy the threshold cleanliness level, that the portion of the physical environment for which the threshold criteria are satisfied likely was insufficiently cleaned; and in response to determining that the portion of the physical environment for which the threshold criteria are satisfied likely was insufficiently cleaned, sending, by the automated cleaning system, an instruction to a device in the physical environment to cause the device to present a notification that identifies the portion of the physical environment that likely was insufficiently cleaned.

In general, one innovative aspect of the subject matter described in this specification can be embodied in methods that include the actions of detecting, by an automated cleaning system, movement of the person within a physical environment; determining, by the automated cleaning system and using data that represents the movement of the person, that one or more threshold criteria for cleaning at least a portion of the physical environment are not satisfied; and in response to determining that the one or more threshold criteria for cleaning at least the portion of the physical environment are not satisfied, determining to skip i) analysis of video data for the physical environment, ii) detection of one or more first areas of the physical environment that have likely been cleaned sufficiently, iii) detection of one or more second areas of the physical environment that have not likely been cleaned sufficiently, iv) sending an instruction to a device in the physical environment to cause the device to present a notification that identifies the portion of the physical environment that likely was insufficiently cleaned, or v) a combination of two or more of these.

In some implementations, instead of detecting the one or more areas of the physical environment that have likely been cleaned sufficiently and determining that the one or more areas of the physical environment that have likely been cleaned sufficiently do not include the portion of the physical environment for which the threshold criteria are satisfied, the automated cleaning system can detect one or more areas of the physical environment that have not likely been cleaned sufficiently and determining that the one or more areas of the physical environment that have not likely been cleaned sufficiently include the portion of the physical environment for which the threshold criteria are satisfied. In response to determining that the one or more areas of the physical environment that have not likely been cleaned sufficiently include the portion of the physical environment for which the threshold criteria are satisfied, the automated cleaning system can send an instruction to a device in the physical environment to cause the device to present a notification that identifies the portion of the physical environment that likely was insufficiently cleaned.

Other embodiments of this aspect include corresponding computer systems, apparatus, computer program products, and computer programs recorded on one or more computer storage devices, each configured to perform the actions of the methods. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The foregoing and other embodiments can each optionally include one or more of the following features, alone or in combination. In some implementations, any of the above implementations can include features from one or more of the other above implementations.

In some implementations, the method can include, after sending the instruction to the device, determining that a threshold likelihood of decontaminating at least the portion of the physical environment is satisfied; and in response to determining that the threshold likelihood of decontaminating at least the portion of the physical environment is satisfied, sending a second instruction to the device to cause the device to halt the cleaning process.

In some implementations, sending the instruction can include sending, by the automated cleaning system and to the device to cause the device to initiate the cleaning process, the instruction to the device that will present a warning that indicates an active self-sanitization cycle, a message that indicates when the device is safe to touch again, or both.

In some implementations, the method can include determining, by the automated cleaning system, a type of cleaning required for at least the portion of the physical environment; and selecting, from multiple devices that can clean respective portions of the physical environment, the device using the type of cleaning required. Sending the instruction to the device in the physical environment to cause the device to initiate the cleaning process of at least the portion of the physical environment can be responsive to selecting the device using the type of cleaning required.

In some implementations, determining that the one or more threshold criteria are satisfied can include determining, by the automated cleaning system and using data that represents the movement, that there is at least a threshold likelihood that a person will move to a physical area that includes the portion of the physical environment; and determining, by the automated cleaning system, that there is not likely another person in the physical area that includes the portion of the physical environment. Sending the instruction can include sending the instruction to the device to cause the device to initiate a cleaning process that will likely finish before the person will likely move to the physical area that includes portion of the physical environment.

In some implementations, the method can include determining, by the automated cleaning system, one or more properties for the portion of the physical environment; and determining, using the one or more properties for the portion of the physical environment, one or more settings for the device. Sending the instruction to the device can include sending, by the automated cleaning system, the instruction to the device in the physical environment to cause the device to initiate a cleaning process of at least the portion of the physical environment using the one or more settings.

In some implementations, the method can include determining, by the automated cleaning system and using data for the portion of the physical environment, a minimum area for the portion of the physical environment to be cleaned given the one or more threshold criteria for cleaning at least the portion of the physical environment that are satisfied. Sending the instruction to the device can include sending, by the automated cleaning system, the instruction to the device in the physical environment to increase a likelihood that the device will clean the minimum area for the portion of the physical environment without cleaning an area surrounding the portion of the physical environment. Sending the instruction can include sending, by the automated cleaning system, the instruction to the device in the physical environment to cause the device to initiate a cleaning process of only the minimum area for the portion of the physical environment.

In some implementations, the method can include receiving, by the automated cleaning system and from one or more cleaning devices, data that indicates an area within the physical environment that the respective cleaning device likely cleaned. Detecting, by the automated cleaning system, the one or more areas of the physical environment with cleanliness levels that satisfy the threshold cleanliness level can include detecting, by the automated cleaning system, the one or more areas of the physical environment with cleanliness levels that satisfy the threshold cleanliness level using the data, from the one or more cleaning devices, that indicates the area within the physical environment that the respective cleaning device likely cleaned. Receiving the data can include receiving, from the one or more cleaning devices, sensor data that indicates one or more properties of the respective cleaning device while the respective cleaning device cleaned the respective area within the physical environment.

In some implementations, sending the instruction can include sending, by the automated cleaning system, the instruction to the device to cause the device to present the notification that identifies i) the portion of the physical environment that likely was insufficiently cleaned, and ii) one or more recommended cleaning processes for the portion of the physical environment. The method can include determining, by the automated cleaning system, the one or more recommended cleaning processes that minimize an amount of cleaning products required for cleaning the portion of the physical environment that was likely insufficiently cleaned. Sending the instruction can include sending the instruction to cause the device to present the notification that indicates that too much or too little cleaning products were used in the portion of the physical environment.

In some implementations, detecting the one or more areas of the physical environment with cleanliness levels that satisfy the threshold cleanliness level can include detecting, by the automated cleaning system, the one or more areas of the physical environment that have likely been cleaned sufficiently. Determining that the portion of the physical environment for which the threshold criteria are satisfied likely was insufficiently cleaned can include determining, by the automated cleaning system, that the one or more areas of the physical environment that have likely been cleaned sufficiently do not include the portion of the physical environment for which the threshold criteria are satisfied.

In some implementations, detecting the one or more areas of the physical environment with cleanliness levels that satisfy the threshold cleanliness level can include detecting, by the automated cleaning system, one or more areas of the physical environment that have not likely been cleaned sufficiently. Determining that the portion of the physical environment for which the threshold criteria are satisfied likely was insufficiently cleaned can include determining, by the automated cleaning system, that the one or more areas of the physical environment that have not likely been cleaned sufficiently include the portion of the physical environment for which the threshold criteria are satisfied.

In some implementations, determining that one or more threshold criteria for cleaning at least the portion of the physical environment are satisfied can include determining that a person was likely in the physical environment for at least a threshold period of time. Determining that one or more threshold criteria for cleaning at least the portion of the physical environment are satisfied can include determining that the portion of the physical environment was not cleaned since the detection of the movement of the person within the physical environment.

The subject matter described in this specification can be implemented in various embodiments and may result in one or more of the following advantages. In some implementations, the methods and systems in this document can reduce a likelihood that a pathogen will be transmitted from one person in a physical environment to another person in the physical environment. For instance, the methods and systems described in this document can detect a likely location for pathogens that might be left by a first person and perform one or more automated actions to increase a likelihood of decontamination of those pathogens. In some implementations, the methods and systems described in this document can detect an area of a physical environment that was likely insufficiently cleaned, e.g., and might still have pathogens, and perform one or more automated cleaning operations for that area, provide a recommendation that identifies that area as likely insufficiently cleaned, or both. In other instances, the methods and systems described in this document can detect specific items that a previous person interacted with such as a coffee maker, a specific cabinet, sink knobs, a microwave, pens, pencils, or other items on a desk, that then need to be cleaned. For example, the item may be a point of sale machine, an automated teller machine, an access panel keypad, or door handles, etc. The methods and systems can initiate a cleaning process for the detected items with which the previous person interacted.

In some implementations, the methods and systems described in this document and reduce energy usage, computational resource usage, or both. For instance, instead of always initiating a cleaning process, or sending instructions to a device to cause presentation of a notification, the methods and systems described in this document, e.g., an automated cleaning system, can determine that threshold criteria are not satisfied and then determine to skip initiation of a cleaning process, skip sending instructions to a device to cause the device to present a notification, or both. In some examples, the methods and systems described in this document can determine that threshold criteria are not satisfied and then stop further analysis of a physical environment, video data, or both. This can reduce use of computer processor, memory, network, or a combination of these.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
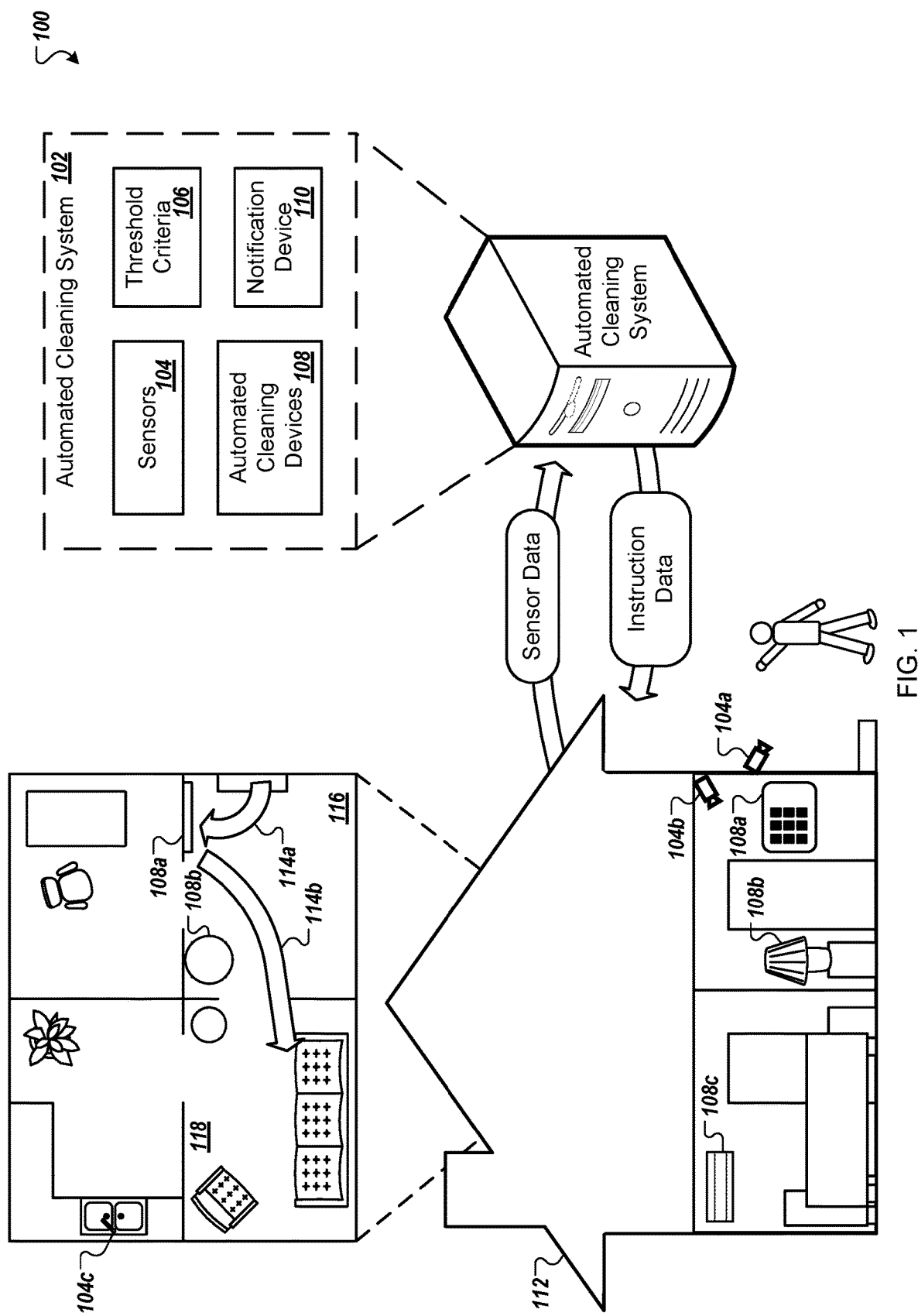
FIG. 1 is an example of an environment in which an automated cleaning system can determine whether to perform an automated cleaning action.

FIG. 1 is an example of an environment 100 in which an automated cleaning system 102 can determine whether to perform an automated cleaning action. For instance, the automated cleaning system 102 receives data from one or more sensors 104. The automated cleaning system 102 can analyze the sensor data to determine whether the sensor data satisfies one or more threshold criteria 106.

The sensors 104 can be part of the automated cleaning system 102 or separate from the automated cleaning system 102. For instance, the automated cleaning system 102 can be located at a first physical location that is remote from a premises 112 at a second physical location that includes the sensors 104a-b. In some examples, the automated cleaning system 102 is located at the same physical location as the premises 112. The premises 112 can be any appropriate premises, such as a home, an office, a school, a hospital, or a theater.

The sensors 104 collect sensor data from one or more areas of the premises 112. The sensors 104 can include any appropriate types of sensors. Some examples of sensors 104 include cameras, motion sensors, touch sensors, heat sensors, global positioning system ("GPS") sensors, sensors included in a mobile tracking device, e.g., a drone, or a door sensor. For instance, the sensors 104 can include a first camera 104a that monitors an exterior of the premises 112. The sensors 104 can include a second camera 104b, or a motion sensor, that monitors an interior of the premises 112. In another instance, a door sensor may detect when a door was opened or closed, implying the door handle might need to be cleaned. A door sensor specifically used on a bathroom stall may indicate that a stall was used, and needs to be cleaned via ultraviolet light, or some other cleaning method. The door sensor in a bathroom would be more permissible than other types of sensors, e.g., a camera, in the bathroom and maintain privacy.

In some examples, the sensors 104 can include sensors that are integrated into another device. For example, the sensors 104 can include a touch sensor that is part of a security control panel 108a. The security control panel 108a can include a touch sensor as part of a touch screen display, a touch sensor in each of one or more buttons included in the security control panel 108a, or both. The sensors 104 can include an activation sensor or a touch sensor in a lamp 108b or a sink faucet 104c.

The automated cleaning system 102 can include an analytics device that analyzes at least some of the sensor data captured by the sensors 104. The analytics device can detect, using the sensor data, movement through the premises 112. This movement through the premises can include interaction with one or more devices 108a-b at the premises, such as when a person turns on a lamp 108b or interacts with the security control panel 108a.

The movement through the premises 112 can be by any appropriate entity. For instance, the analytics device can determine whether a person is moving through the premises 112, whether an animal is moving through the premises 112, or both. In some examples, the analytics device can detect movement and need not detect the type of entity that moved. For instance, the analytics device need not distinguish between movement by a person and movement by an animal, such as a dog. Although this document generally refers to examples of a person moving through a premises or a physical environment, the same examples can apply to something else moving through the premises or the physical environment, such as an animal, e.g., a dog, moving through a premises.

The analytics device can use any appropriate processes to analyze the sensor data and detect movement through the premises 112. For instance, the analytics device can include one or more machine learning models that analyze image data and output values that indicate whether movement was detected at the premises.

The automated cleaning system 102 determines whether the sensor data satisfy one or more threshold criteria 106. The threshold criteria can include whether movement was detected, whether a person detected by the sensors 104 was likely sick, other appropriate threshold criteria, or a combination of two or more of these.

The automated cleaning system 102 can determine whether a person was likely sick, e.g., whether sensor data for the person satisfy a threshold criteria that the person is likely sick, using image data for the person, temperature data for the person, other appropriate data for the person, or a combination of these. For instance, the first camera 104a can capture a first image of a person approaching the premises 112 who uses a tissue. The second camera 104b can capture a second image of the person sneezing while inside the premises 112. The automated cleaning system 102 can analyze the first image and the second image and determine that the sensor data for the person satisfy the threshold criteria that the person is likely sick.

When the sensor data do not satisfy the one or more threshold criteria 106, the automated cleaning system 102 can determine to skip performing another action based on the sensor data. For instance, the automated cleaning system 102 can determine to skip activating an automated cleaning device 108, providing a notification for presentation on a notification device 110, or both. The automated cleaning system 102 can then analyze additional sensor data and compare the additional sensor data to the one or more threshold criteria 106.

When the sensor data satisfy the one or more threshold criteria 106, the automated cleaning system 102 can initiate an automated process for a premises 112. The automated process can include the automated cleaning system 102 activating an automated cleaning device 108, providing a notification for presentation on a notification device 110, or a combination of both. Some examples of automated cleaning devices 108 can include a self-cleaning security control panel 108a, a self-cleaning lamp 108b, an HVAC system 108c, e.g., represented by a vent, an infrared light, e.g., that can heat an area to decontaminate pathogens, an ultraviolet light, or an automated vacuum.

For example, the automated cleaning system 102 can determine a path 114a-b of the person while they were at the premises 112 or in a portion of the premises 112. The portion of the premises can include a foyer 116, a living room 118, or both. The path can be an entire path taken by the person at the premises 112, e.g., the paths 114a-b, or a portion of the patent taken by the person at the premises 112, e.g., a first path in a foyer 116 or a second path in a living room 118. The portion of the premises 112 can be any appropriate portion of any type of premises, such as an office building, a hospital, or a school. Some other examples of portions of a premises 112 can include a hallway, a kitchen, a dining area, a restroom, or an elevator.

Figure 2A:
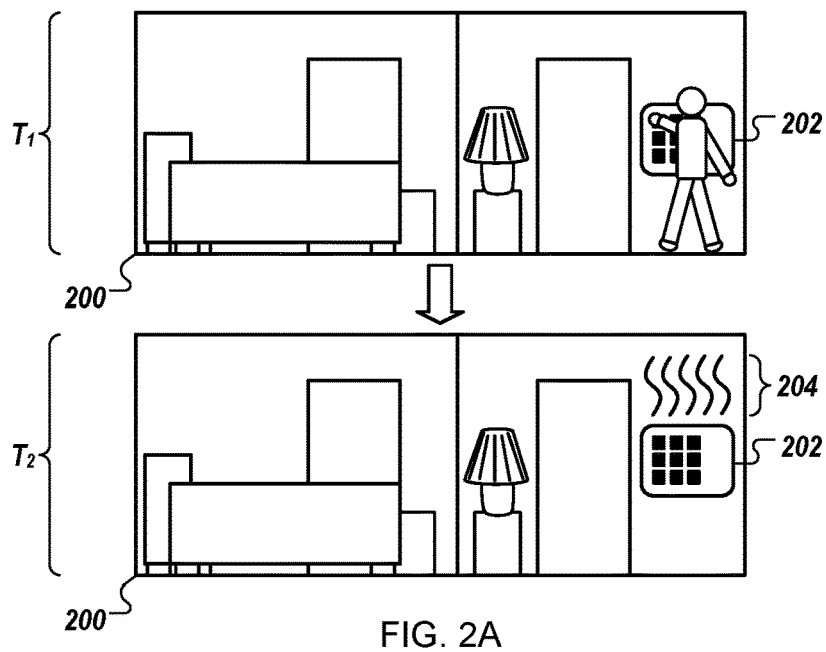
FIGS. 2A-B depict various automated cleaning devices that can receive the instruction data from the automated cleaning system and clean portions of a premises.
Figure 2B:
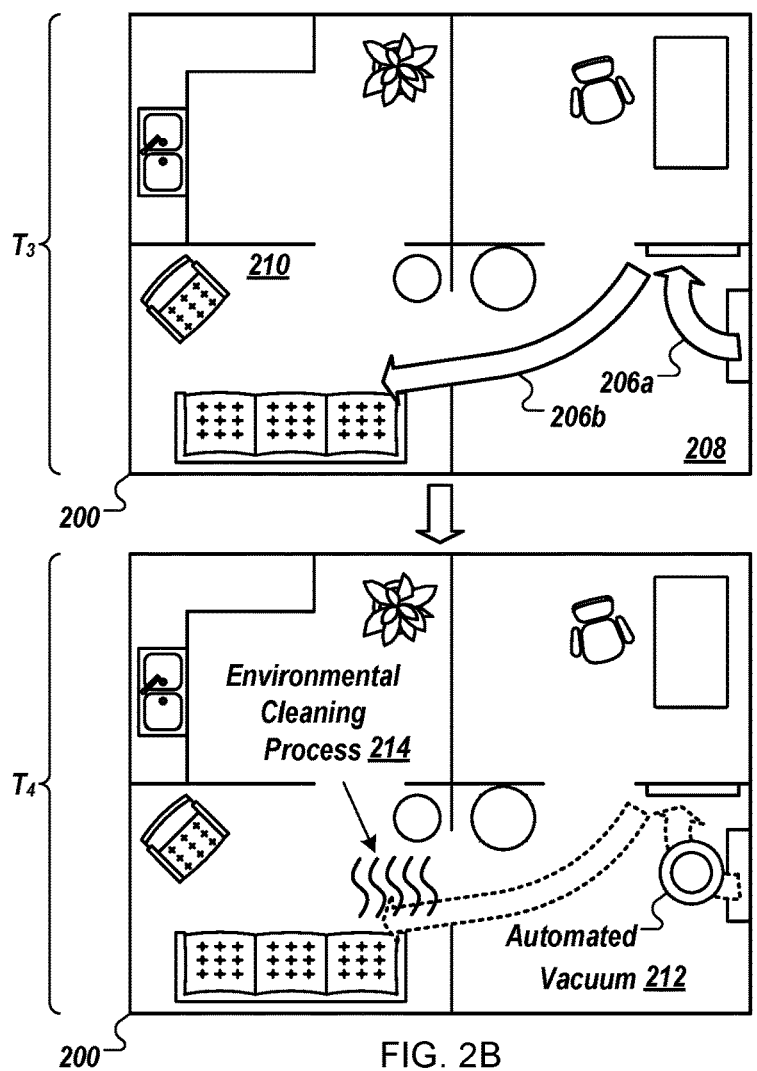

The automated cleaning system 102 can use data for the path 114a-b to determine instruction data for one or more automated cleaning device 108. Upon receipt of the instruction data, the automated cleaning devices 108 can clean some of the premises 112 as indicated by the instruction data. FIGS. 2A-B depict various automated cleaning devices that can receive the instruction data from the automated cleaning system 102 and clean portions of a premises 200, e.g., the premises 112.

In FIG. 2A, a security control panel 202, e.g., the security control panel 108a, initiates a self-cleaning process upon receiving instruction data from the automated cleaning system 102. For instance, when a person interacts with the security control panel 202 during time period $T_1$, the security control panel 202, or another component of the automated cleaning system 102, can determine the areas of the security control panel 202 with which the person interacted or likely interacted. The security control panel 202 can determine areas of the panel with which the person interacted or likely interacted using one or more touch sensors included in the panel. This can include a touch sensor for a touch screen, a button, or both. Another component of the automated cleaning system 102 can determine areas of the security control panel 202 with which the person likely interacted using a camera or a motion sensor. The camera or the motion sensor can have a field of view that includes at least part of the security control panel 202.

The security control panel 202 can determine areas of the panel with which the person likely interacted using data that indicates areas with which the person actually interacted. For instance, the security control panel 202 can include a first sensor in a first button of the panel and not include a sensor in a second button that is close to the first button. When the security control panel 202 detects, using the first sensor, interaction with the first button, the security control panel 202 can determine that the person likely interacted with the second button given the distance between the two buttons.

During time period $T_2$, the security control panel 202 can initiate a self-cleaning process to increase a likelihood that any pathogens on the security control panel 202 are decontaminated. This can occur in response to the security control panel 202 receiving the instruction data, e.g., from the automated cleaning system. In some examples, a component in the security control panel 202 can receive the instruction data from another component in the security control panel 202, e.g., as part of the automated cleaning system. For instance, a controller in the security control panel 202 can generate the instruction data upon determining to initiate a self-cleaning process and a cleaning element can receive the instruction data.

As part of the self-cleaning process, the security control panel 202 can enable one or more cleaning elements that are integrated in the security control panel 202. A cleaning element can be, for example, a heat coil that increases a temperature 204 of a portion of the security control panel 202. The heat coil can increase the temperature 204 based on a potential pathogen type that could be on the security control panel 202, a duration for which the heat coil will be enabled, or both. For example, when the security control panel 202 will likely be used within a first threshold time period, the security control panel 202 can enable the heat element to a first, higher temperature 204 for a first, shorter time period. When the security control panel will not likely be used within the first threshold time period, the security control panel 202 can enable the heat element to a second, lower temperature 204 for a second, longer time period.

The security control panel 202, or the automated cleaning system, can dynamically select the temperature 204, the time period during which the cleaning elements will be enabled, or both. In some implementations, the security control panel 202 can select the temperature 204, the time period, or both, using data for a person for whom there is a threshold likelihood of using the security control panel 202. For instance, the security control panel 202 can select a higher temperature 204, a longer time period, or both, for a person who is more likely to get sick, e.g., a person who is immunocompromised, and can select a lower temperature 204, a shorter time period, or both, for a person who is less likely to get sick, e.g., a person who is not immunocompromised.

In some examples, the security control panel 202 can select the temperature 204, a duration of the time period, or both, using an amount of energy available to the security control panel 202. For example, when the security control panel 202 has a substantially constant energy source, e.g., is hardwired into the electrical system for the premises 200, the security control panel 202 can select a higher temperature 204, a longer time period, or both. When the security control panel 202 has a limited energy source, e.g., is battery powered, or that energy source is less than a threshold amount, e.g., less than fifty percent, the security control panel 202 can select a lower temperature, e.g., that uses less energy. In some examples, although the security control panel 202 has a limited energy source, the security control panel 202 can select a longer time period or a shorter time period depending on other factors, such as the potential pathogen type, a type of person for whom there is a threshold likelihood of using the security control panel 202, or other appropriate factors.

In some implementations, an automated cleaning system can use a cleaning type when determining a device to clean a portion of an environment, e.g., the premises 200. Types of cleaning can include cleaning a floor, cleaning a rug, cleaning a button, ultraviolet cleaning, vacuuming, disinfecting, or a combination of these.

For instance, an automated cleaning system can determine that a person walked across a floor at the premises 200 and touched the security control panel 202. The automated cleaning system can use data for the floor, the security control panel 202, or both, to determine the device. When the automated cleaning system determines that the portion of the environment would either require two devices to separately clean two objects in the portion, e.g., the floor and the security control panel, or a single device, e.g., an ultraviolet light, the automated cleaning system can use data for the cleaning types to determine to send an instruction to the single device instead of two separate devices, e.g., an automated vacuum and the security control panel 202. The automated cleaning system can use other parameters, such as an expected time at which the portion of the environment will be used again, a duration for the cleaning type, or both, when determining a device from multiple devices to use to clean the portion of the environment.

In FIG. 2B, one or more automated cleaning devices receive instruction data from the automated cleaning system for a path 206a-b on which the person likely moved through the premises 200. For instance, during time period $T_3$, the automated cleaning system can receive sensor data from one or more cameras. The sensor data can include images that depict the person walking through the premises 200 along a path 206a-b. This can include the person entering into a foyer 208 and then walking along the path 206b from the foyer 208 into a living room 210. In some examples, the path 206a-b is a person's likely path, e.g., when the sensor data on which the instructions are based is partially occluded, such as when a camera's view of the person is partially blocked by a plant.

The automated cleaning system can send instruction data to one or more automated cleaning devices 212-214 based on the path 206a-b of the person's movement through the premises 200. For instance, the automated cleaning system can determine that one or more threshold criteria are satisfied that indicate that at least a portion of the premises 200 should be cleaned. In response, the automated cleaning system can send instruction data to the automated cleaning devices 212-214.

In response to receipt of the instruction data, and during time period $T_4$, the automated cleaning devices 212-214 can begin an automated cleaning process. This can include an automated vacuum 212 cleaning an area around the path 206a-b. The instruction data can identify the path 206a-b, the areas of the premises for the automated vacuum 212 to clean, or both. When the instruction data identifies the path 206a-b, the automated vacuum 212 can analyze first data for the path 206a-b and second data for the premises 200 to determine which areas within a threshold distance from the path 206a-b to clean. This can include the automated vacuum 212 determining which areas within the threshold distance from the path 206a-b the automated vacuum 212 is able to clean, e.g., when the automated vacuum 212 cannot clean a couch. In some examples, another portion of the automated cleaning system can perform this analysis, e.g., of what areas of the premises 200 the automated vacuum 212 should clean. This can reduce computer resource usage, energy usage, or both, by having a single component perform the analysis and send instructions to various devices rather than having each device perform the analysis separately.

During the time period $T_4$, an automated cleaning device 214, e.g., an HVAC system, can initiate an environmental cleaning process of at least a portion of the premises 200. This can include the HVAC system increasing or decreasing a humidity level at the premises or within a portion of the premises, e.g., the living room 210. This can include the HVAC system increasing or decreasing a temperature at the premises or within a portion of the premises, e.g., the living room 210. The automated cleaning system, or the automated cleaning device, can determine whether to increase or decrease the humidity or the temperature based on a potential pathogen in the premises 200.

In some examples, during the time period $T_4$, a different type of automated cleaning device 214, other than an HVAC system, can initiate the environmental cleaning process. For example, an infrared light can increase a temperature of a portion of the premises 200 to increase a likelihood that any pathogens in the portion are decontaminated.

Although the examples described here are for areas within a premises 200, e.g., within a physical environment, the automated cleaning system can initiate an automated cleaning process anywhere at a physical environment. For instance, the automated cleaning system can initiate an automated cleaning process at a portion of a physical environment that is outside the premises 200. This can include initiating an automated cleaning process for an exterior door handle of a front door through which a person passed, a handle for a gate in a fence surrounding the premises 200, a bench or chair outside the premises 200, or another appropriate portion of a physical environment.

Figure 3:
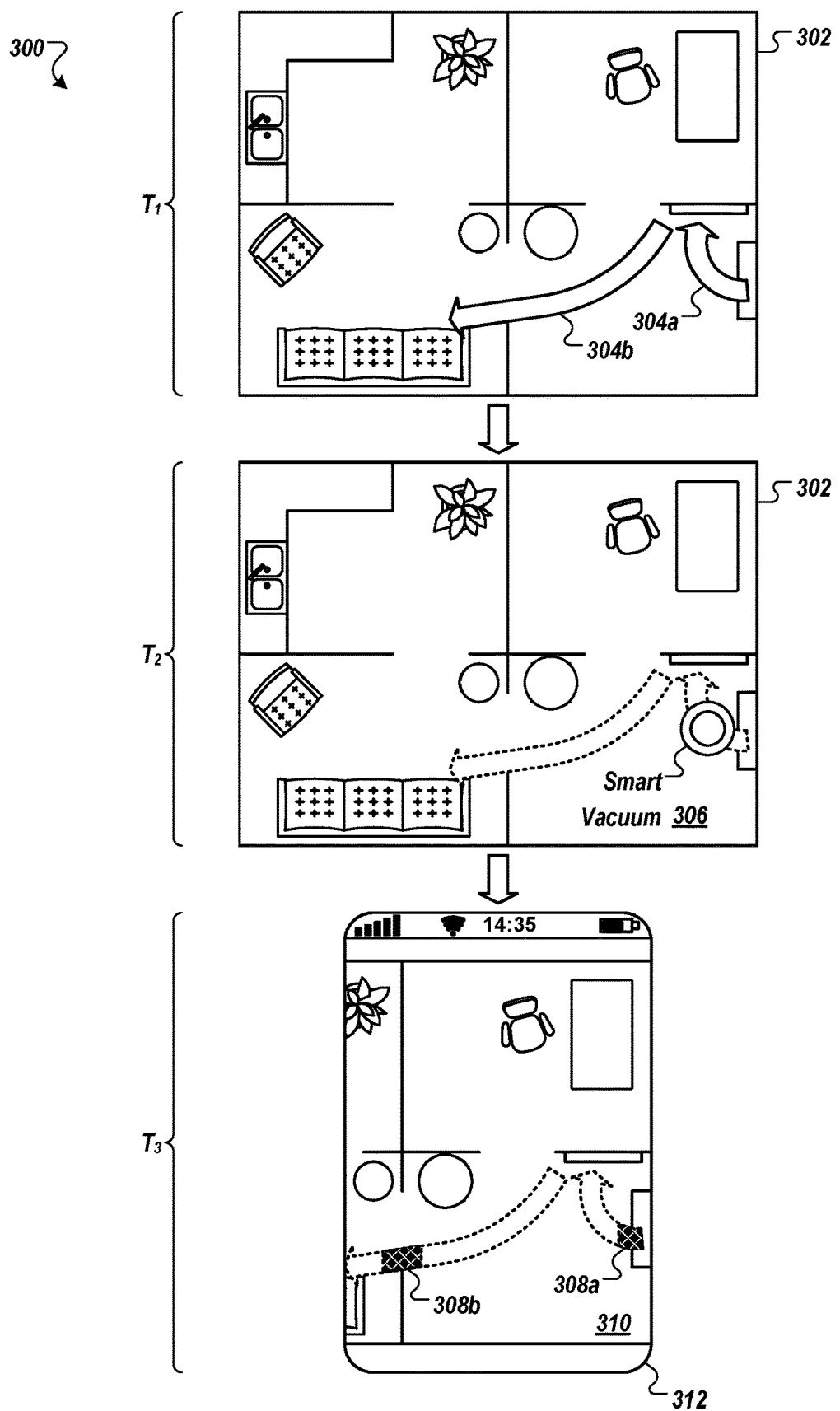
FIG. 3 depicts an example environment in which an automated cleaning system provides a notification that identifies areas of a premises that were likely insufficiently cleaned.

In some implementations, the automated cleaning system can provide a notification for presentation on a notification device, instead of or in addition to providing instruction data to an automated cleaning device. FIG. 3 depicts an example environment 300 in which an automated cleaning system provides a notification that identifies areas of a premises 302 that were likely insufficiently cleaned.

For example, the automated cleaning system can determine which areas of a premises 302 likely have been cleaned, or have been sufficiently cleaned, and which areas of the premises 302 likely have not been cleaned, or have been insufficiently cleaned. The automated cleaning system can then generate a notification that identifies the areas of the premises 302 that likely have been insufficiently cleaned. Areas that likely have been insufficiently cleaned can include areas that likely have not been cleaned. The notification can include a recommended path to clean the identified areas, or other appropriate information about the identified areas.

In some examples, the automated cleaning system can, during a time period $T_1$, can determine a path 304a-b of a person through the premises 302. The automated cleaning system can use data from one or more sensors, such as a camera, to determine the path 304a-b of the person through the premises 302. For instance, as described above, the automated cleaning system can receive images from the camera, analyze the images using video analytics, and determine the path 304a-b using the result of the analysis.

During time period $T_2$, the automated cleaning system can determine one or more portions of the premises that were likely cleaned after the person moved through the premises along the path 304a-b, that were likely not cleaned, or both. Although the examples described here generally refer to detection of areas that were likely cleaned, the examples can similarly apply to detection of areas that were likely not cleaned, or detection of both areas that were likely cleaned and areas that were likely not cleaned.

For instance, the automated cleaning system can use sensor data from one or more cleaning devices, one or more cameras, other appropriate sensors, or a combination of two or more of these, to determine the portions of the premises 302 that were likely cleaned. Some examples of sensor data received from a cleaning device, e.g., a smart cleaning device such as a vacuum 306, are described in more detail below. In some examples, the automated cleaning system can use video analytics to determine the portions of the premises 302 that were likely cleaned, e.g., similar to the video analytics used to determine the path 304a-b. In some examples, the automated cleaning system can use data from one or more automated cleaning devices to determine the portions of the premises 302 that were likely cleaned.

The automated cleaning system can use data that indicates the portions of the premises 302 that were likely cleaned to determine other portions 308a-b of the premises 302 that were likely not cleaned, were potentially insufficiently cleaned, or both. In some examples, the automated cleaning system can use data that indicates portions of the premises 302 that were likely not cleaned or were likely not cleaned sufficiently. A portion that was likely not cleaned sufficiently can include an area that was likely not cleaned. These other portions 308a-b can generally be referred to as portions 308a-b of the premises 302 that likely need additional cleaning or were likely insufficiently cleaned.

For example, the automated cleaning system can determine that a first portion 308a of the premises 302 was likely not cleaned, e.g., because the smart vacuum 306 could not access the first portion 308a. The automated cleaning system can determine that a second portion 308b of the premises 302 was potentially insufficiently cleaned, e.g., because the smart vacuum 306 went over the second portion 308b for less than a threshold period of time.

During time period $T_3$, the automated cleaning system provides a notification to a device 312 that indicates the portions 308a-b that likely need additional cleaning or were likely insufficiently cleaned. The notification can include instruction data that causes the device 312 to present a user interface 310 that depicts the portions 308a-b that likely need additional cleaning or were likely insufficiently cleaned. The user interface 310 can depict the path 304a-b of the person who went through the premises; the types of cleaning that were performed to increase a likelihood that any pathogens left by the person have been removed, decontaminated, or both; or a combination of these. In some examples, the user interface 310 can depict information about the person who went through the premises, e.g., actions that the person performed, whether the person sneezed, or other appropriate information about the person.

The automated cleaning system can provide a notification that generates an audible presentation, a visible presentation, or both, for a user. For instance, the automated cleaning system can provide the notification to the device 312 that causes the device 312 to audibly indicate, to a person within listening distance of the device 312, that additional cleaning may be necessary. The notification can indicate the portions 308a-b of the premises that likely need additional cleaning, types of cleaning that should be performed on those portions 308a-b, or both.

In some implementations, the automated cleaning system can provide a notification to the device to reduce a likelihood that a portion of the premises 302 is not sufficiently cleaned. For instance, a cleaning person might oversee an area that requires cleaning, whether based on the path 304a-b of another person who went through the premises 302 or for general cleaning of the premises 302.

The automated cleaning system can analyze sensor data from multiple sensors to determine the portions 308a-b that likely need cleaning or were likely insufficiently cleaned. For example, the automated cleaning system can analyze video data captured by a camera and other sensor data captured by cleaning equipment to enhance the system's understanding of the portions of the premises 302 that were disinfected or cleaned. The cleaning equipment can connect to a network, e.g., the Internet or a local area network, or another communication medium to provide the automated cleaning system with the other sensor data.

When the cleaning equipment is being used, the cleaning equipment can provide data to the automated cleaning system. The data can include sensor data, data about a mode of operation for the cleaning equipment, or both. For instance, the cleaning equipment can include a smart mop, a smart spray bottle, or a smart fumigator, that includes an activation switch that indicates whether the cleaning equipment is engaged in cleaning activities. In some examples, the cleaning equipment can include a sensor that indicates when the cleaning equipment is engaged in cleaning activities, e.g., when a smart spray bottle dispenses liquid. When the cleaning equipment is engaged in cleaning activities, the cleaning equipment can send a signal to the automated cleaning system that indicates the cleaning equipment's engagement in cleaning activities. The activation switch can be "on" to indicate engagement, and similarly turned "off" to indicate a lack of engagement, in response to user interaction with the activation switch. The signal can indicate one or more settings for the cleaning equipment, such as a power level, a cleaning mode, a dispensing mode, or other appropriate cleaning equipment settings.

When the automated cleaning system, e.g., a camera or another computer in the system, receives the signal that indicates that the cleaning equipment is engaged in cleaning activities, the automated cleaning system can track the cleaning equipment. The automated cleaning system can use the signal and other data for the cleaning equipment to track the cleaning equipment. For example, the automated cleaning system can capture, as the other data, an image that depicts a visual indicator for the cleaning equipment or one or more wireless signals (e.g., radar, Wi-Fi, Bluetooth, Connectivity Standards, or Matter) that can be used to determine a position for the cleaning equipment.

When using a visual indicator, the automated cleaning system can use a sequence of images that each depict the visual indicator to determine the portions of the premises 302 that have likely been cleaned. The visual indicator can include a color or a pattern. The color or pattern can be specific to a type of cleaning equipment. For example, a smart broom might have a bright yellow cap, or a smart spray bottle might have a black and white striped pattern along its barrel. In some examples, cleaning equipment can have a visual indicator that is reflective or emissive in an infrared spectrum that can be detected by a camera's infrared functionality.

In some implementations, a smart spray bottle, or other fluid dispensing cleaning equipment, can determine a recommended amount of cleaning fluid to dispense. This can reduce waste of cleaning fluid, reduce a likelihood that an insufficient amount of cleaning fluid is dispensed, or both. The fluid dispensing cleaning equipment can determine the recommended amount of cleaning fluid to dispense using a message received from the automated cleaning system.

Smart fluid dispensing equipment can include a smart spray bottle, in addition to other types of fluid dispensing equipment. The smart fluid dispensing equipment can include one or more sensors. For instance, the smart fluid dispensing cleaning equipment can include a sensor that detects a volume of fluid expelled by the smart fluid dispensing cleaning equipment. The smart fluid dispensing cleaning equipment can include a sensor that determines an orientation of the cleaning equipment, e.g., when fluid is dispensed.

When engaged, the smart fluid dispensing cleaning equipment can send a signal to the automated cleaning system. The signal can indicate information about the force, density, liquid volume, range, or a combination of these, of the smart fluid dispensing cleaning equipment. For example, a smart fumigator can send a signal that indicates configuration settings such as the volume of fluid to be expelled, pressure on the fluid, or both. The signal can indicate information about the smart fluid dispensing cleaning equipment's orientation when engaged. The orientation can be with respect to a reference orientation, a cardinal point, e.g., in degrees, or another appropriate orientation. The signal can indicate information about the smart fluid dispensing cleaning equipment's liquid capacity, e.g., as the amount of liquid in the smart fluid dispensing cleaning equipment's tank changes over time.

The automated cleaning system can receive the signal and use the signal to track the smart fluid dispensing cleaning equipment's location within the premises 302. The automated cleaning system can use the data from the signal to determine portions of the premises 302 that were likely cleaned, an extent of the cleaning, or both. For instance, the automated cleaning system can use localization information about the smart fluid dispensing cleaning equipment's position and signal data to determine the density of cleaning product applied to a portion of the premises 302. This can include the automated cleaning system using the smart fluid dispensing cleaning equipment's orientation to determine a direction in which fluid was likely dispensed. The automated cleaning system can use the force, density, or both, of dispensation; the volume of liquid dispensed; or both, to determine the area over which the liquid was likely dispensed, e.g., given the corresponding orientation.

The automated cleaning system can then provide the smart fluid dispensing cleaning equipment, or another device, with a notification that indicates that too much or too little fluid has been dispensed. For instance, the automated cleaning system can use data for a smart fluid dispensing cleaning equipment, e.g., the received signal and location data, to determine that a particular portion of the premises 302 was likely insufficiently cleaned. The receiving device can then present a notification on a display that indicates where additional fluid should be dispensed.

When the automated cleaning system determines that too much fluid was likely dispensed, the automated cleaning system can send a notification to a device that indicates this. For example, the receiving device can indicate, in a user interface or audibly, that too much fluid was likely dispensed. In some examples, the smart fluid dispensing cleaning equipment can use the notification from the automated cleaning system to automatically disable fluid dispensation when an appropriate threshold is satisfied while the smart fluid dispensing cleaning equipment does not change orientation or a position within the premises 302.

In some implementations, the automated cleaning system can generate a report for presentation in a user interface that indicates a recommended density of cleaning fluid used to satisfy a threshold likelihood of decontamination of pathogens likely in the premises 302. The automated cleaning system can provide data for the report to a device to cause presentation of the user interface on a display. The report can indicate, for example, that the sprayer is ⅓ empty after cleaning an area that was only expected to take 1/10 of the tank, to reduce a likelihood of continued overuse of the cleaning fluid. In some examples, the report can indicate which areas need to be re-cleaned due to a low density of cleaning fluid, indicate areas that might be unsafe or need additional time to dry due to the over-application of cleaning fluid, or both.

With respect to FIGS. 1-3 in general, the automated cleaning system 102 is an example of a system implemented as computer programs on one or more computers in one or more locations, in which the systems, components, and techniques described in this document are implemented. The notification device 110, the device 312, or both, may include personal computers, mobile communication devices, displays, e.g., a television, speakers, and other devices that can send and receive data over a network. The network (not shown), such as a local area network (LAN), wide area network (WAN), the Internet, or a combination thereof, connects the device 312, and the automated cleaning system 102. The automated cleaning system 102 may use a single server computer or multiple server computers operating in conjunction with one another, including, for example, a set of remote computers deployed as a cloud computing service.

The automated cleaning system 102 can include several different functional components, including the analytics device, the automated cleaning devices 108, and the notification device 110. The analytics device, the automated cleaning devices 108, the notification device 110, or a combination of these, can include one or more data processing apparatuses. For instance, each of the analytics device, the automated cleaning devices 108, and the notification device 110 can include one or more data processors and instructions that cause the one or more data processors to perform the operations discussed herein.

The various functional components of the automated cleaning system 102 may be installed on one or more computers as separate functional components or as different modules of a same functional component. For example, the analytics device can be implemented as computer programs installed on one or more computers in one or more locations that are coupled to each through a network. In cloud-based systems for example, these components can be implemented by individual computing nodes of a distributed computing system.

Figure 4:
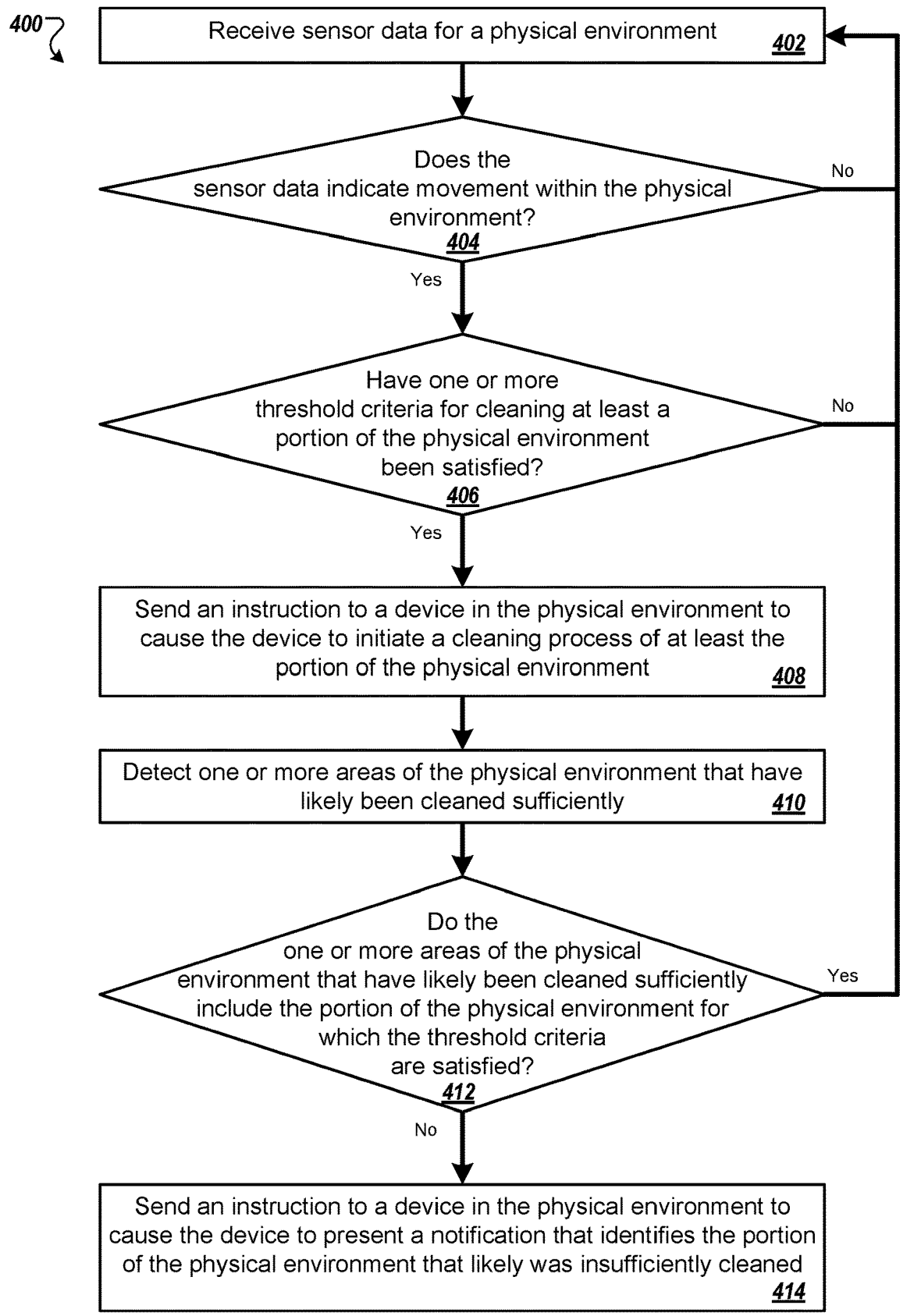
FIG. 4 is a flow diagram of a process for determining whether to clean a portion of a physical environment.

FIG. 4 is a flow diagram of a process 400 for determining whether to clean a portion of a physical environment. For example, the process 400 can be used by the automated cleaning system 102 from the environment 100.

An automated cleaning system receives sensor data for a physical environment (402). For example, the automated cleaning system receives the sensor data, e.g., an image, from a camera. When the automated cleaning system detects movement in the physical environment, the automated cleaning system can cause a device, e.g., a drone, to monitor the movement. The automated cleaning system can receive the sensor data from the device.

The automated cleaning system determines whether the sensor data indicates movement within the physical environment (404). For instance, the automated cleaning system analyzes the sensor data to determine whether the sensor data indicates movement within the physical environment. The automated cleaning system can use analytics, e.g., video analytics, when making this determination.

The automated cleaning system can perform one or more steps depending on what the sensor data indicates. In some examples, in response to determining that the sensor data does not indicate movement within the physical environment, the automated cleaning system can receive, or wait to receive, additional sensor data. For example, the automated cleaning system can proceed to step 402. In some examples, the automated cleaning system can determine to skip one or more steps in the process 400, e.g., and proceed to step 402. The automated cleaning system can skip one or more of steps 406, 408, 410, 412, or 414.

In response to determining that the sensor data indicates movement within the physical environment, the automated cleaning system determines whether one or more threshold criteria for cleaning at least a portion of the physical environment have been satisfied (406). For example, the automated cleaning system can determine, using data that represents the movement, whether the one or more threshold criteria for cleaning at least a portion of the physical environment are satisfied.

The threshold criteria can be any appropriate threshold criteria. For instance, the threshold criteria can include whether a person is wearing a mask; whether the person coughed or sneezed; whether the person has a temperature, e.g., a skin temperature, that satisfies a threshold temperature; whether the person is wearing other personal protective equipment; whether the person is in a portion of the physical environment for which particular rules apply; or a combination of two or more of these.

The automated cleaning system can perform one or more steps depending on whether the threshold criteria are satisfied. In some examples, in response to determining that one or more threshold criteria for cleaning at least a portion of the physical environment have not been satisfied, the automated cleaning system can receive, or wait to receive, additional sensor data. For example, the automated cleaning system can proceed to step 402. In some examples, the automated cleaning system can determine to skip one or more steps in the process 400, e.g., and proceed to step 402. The automated cleaning system can skip one or more of steps 408, 410, 412, or 414.

In response to determining that one or more threshold criteria for cleaning at least a portion of the physical environment have been satisfied, the automated cleaning system sends an instruction to a device in the physical environment to cause the device to initiate a cleaning process of at least the portion of the physical environment (408). For instance, the automated cleaning system can send an instruction to an automated cleaning robot, an HVAC system, or an infrared light to cause the corresponding device to initiate a cleaning process of at least the portion of the physical environment.

The automated cleaning system detects one or more areas of the physical environment that have likely been cleaned sufficiently (410). For instance, the automated cleaning system can receive sensor data from one or more devices, whether automated cleaning devices, smart cleaning devices, or other sensors that captured data about other cleaning devices or portions of the physical environment. The automated cleaning system can perform analytics on the received data to detect the one or more areas of the physical environment that have likely been cleaned.

In some implementations, the automated cleaning system can detect one or more areas of the physical environment that likely have not been cleaned sufficiently. The automated cleaning system can perform this analysis instead of or in addition to detecting the one or more areas of the physical environment that have likely been cleaned sufficiently. The automated cleaning system can receive sensor data from one or more devices, e.g., such as the devices described above, to perform this analysis.

The automated cleaning system determines whether the one or more areas of the physical environment that have likely been cleaned sufficiently include the portion of the physical environment for which the threshold criteria are satisfied (412). For example, the automated cleaning system can determine whether additional cleaning for the portion of the physical environment is likely required.

In some examples, when the automated cleaning system detects one or more areas of the physical environment that likely have not been cleaned sufficiently, the automated cleaning system can determine whether the one or more areas that likely have not been cleaned sufficient include the portion of the physical environment for which the threshold criteria are satisfied. The automated cleaning system can use a result of this detection to determine whether additional cleaning for the portion of the physical environment is likely required.

In some implementations, the automated cleaning system can detect one or more areas of the physical environment with cleanliness levels that satisfy a threshold cleanliness level. The threshold cleanliness level can indicate whether an area is likely sufficiently cleaned or not likely sufficiently cleaned.

The automated cleaning system can determine, using data for the one or more areas of the physical environment with cleanliness levels that satisfy the threshold cleanliness level, that the portion of the physical environment for which the threshold criteria are satisfied likely was insufficiently cleaned. For instance, the automated cleaning system can determine using data for the areas that satisfy the threshold cleanliness level whether the portion of the physical environment is likely sufficiently cleaned or not likely sufficiently cleaned.

In response to determining that the portion of the physical environment for which the threshold criteria are satisfied likely was sufficiently cleaned, the automated cleaning system can receive or wait to receive additional sensor data for the physical environment. For example, in response to determining that the one or more areas of the physical environment that have likely been cleaned sufficiently include the portion of the physical environment for which the threshold criteria are satisfied, the automated cleaning system can receive or wait to receive additional sensor data for the physical environment. For example, the automated cleaning system can proceed to step 402.

In response to determining that the portion of the physical environment for which the threshold criteria are satisfied likely was insufficiently cleaned or in response to determining that the one or more areas of the physical environment that have likely been cleaned sufficiently do not include the portion of the physical environment for which the threshold criteria are satisfied, the automated cleaning system sends an instruction to a device in the physical environment to cause the device to present a notification that identifies the portion of the physical environment that likely was insufficiently cleaned (414). A portion of the physical environment that likely was insufficiently cleaned can be a portion that likely was not cleaned or a portion that was not cleaned properly and requires additional cleaning. This can include providing the instruction to the device to cause the device to present a visual, audible, or both, indication of the portion of the physical environment that has not likely been cleaned or otherwise cleaned insufficiently.

The order of steps in the process 400 described above is illustrative only, and determining whether to clean the portion of the physical environment can be performed in different orders. For example, the automated cleaning system can send an instruction to cause a device to present a notification that identifies the portion of the physical environment, e.g., perform step 414, prior to sending the instruction to cause a device to initiate a cleaning process of the portion of the physical environment, e.g., perform step 408.

In some implementations, the process 400 can include additional steps, fewer steps, or some of the steps can be divided into multiple steps. For example, the automated cleaning system can perform steps 402, 406, and 408 without performing any of the other steps in the process 400. The automated cleaning system can perform steps 402, 404, 406, and 408 without performing any of the other steps in the process 400.

In some examples, the automated cleaning system can perform steps 402, 410, 412, and 414 without performing the other steps in the process 400. In some examples, the automated cleaning system can perform steps 402, 404, 406, 410, 412, and 414 without performing the other steps in the process 400. In some examples, the automated cleaning system can perform steps 402, 406, 410, 412, and 414 without performing the other steps in the process 400.

In some implementations, the automated cleaning system can analyze an image to determine whether to perform one or more automated actions for cleaning a physical environment using one or more rules. The rules can include whether a depicted person in the image is wearing a facemask, a likelihood that the person is sick, or both. The automated cleaning system can use a result of this analysis to determine whether, where, or both, cleaning should be performed. For instance, the automated cleaning system can clean physical environments through which a person not wearing a mask or not wearing a mask properly, or with a threshold likelihood of being sick, or both, moved. The automated cleaning system can determine to not perform one or more cleaning actions in a physical environment through which a person wearing a mask, or with less than the threshold likelihood of being sick, or both, moved.

The automated cleaning system can use any appropriate method to determine whether a person is likely wearing a mask or is likely wearing a mask properly. For example, the automated cleaning system can determine that a person is not likely wearing a mask when a face for that person, depicted in an image, includes a mouth, a nose, or both. The automated cleaning system can determine that a person is not likely wearing a mask or not likely wearing a mask properly when, upon detecting the person or the person's head, the automated cleaning system detects one or more facial features. A person who is not likely wearing a mask properly can include people who are not likely wearing a mask.

In some examples, the automated cleaning system can use a classifier to determine when people depicted in images are not likely wearing a mask, are not likely wearing a mask properly, or both. The classifier can be trained to recognize one or more compliant masks, e.g., in a setting where employees are expected to wear masks issued by an employer. The classifier, or another portion of the automated cleaning system, can detect other types of personal protective equipment, such as gloves, hearing protection, hair covers, shoe covers, etc. This data can be used to determine whether, when, or both, cleaning should be performed.

In some examples, the automated cleaning system can determine that a person in a camera's field of view is wearing a mask, is not wearing a mask, or that mask wearing cannot be confirmed (at present) given the available view of the person. The automated cleaning system can make this determination with it a confidence level that represents the likelihood the person is or is not wearing a mask, or that mask wearing cannot be confirmed. If the person's face is not currently visible, the automated cleaning system can infer that the person is or is not wearing a mask using data for the most recent image or images of a video sequence in which the person's face was visible, when the person's face was most clearly visible, or when the confidence of the decision was above a predetermined threshold.

In some implementations, the automated cleaning system can use pose analysis when determining whether to perform a cleaning action. For instance, the automated cleaning system can use pose information for a person to determine whether an image captured by a camera should likely depict a masked part of the person's face. The automated cleaning system can use pose information to determine whether a depiction of a person in an image indicates that the person's face is likely obscured by a hand, an arm, an object held in the hand, or other body part, rather than by a mask.

In some examples, the automated cleaning system can determine whether a person might be donning or doffing a mask. For example, if a first image depicts a person wearing a mask, and a second image depicts the person turning away from the camera but the automated cleaning system does not detect the person's hands near the person's face or head, the automated cleaning system can infer that the person is likely still wearing the mask.

In some implementations, the automated cleaning system can use a determination whether a person is likely wearing a mask as input to a more complex rule, to change parameters of a rule, or both. For instance, the automated cleaning system can determine whether an unmasked person enters a mask required area. If the unmasked person does not, e.g., if the person remains in their own office, the automated cleaning system can determine to skip performing an action. When the automated cleaning system determines that the unmasked person enters a mask required area, or remains in a mask required area for more than a threshold amount of time, the automated cleaning system can determine to perform an action in response. In some implementations, the automated cleaning system can determine to perform an action when two masked people come within six feet of each other, or an unmasked person comes within twelve feet of anyone.

Some examples of actions performed by the automated cleaning system, in addition to or instead of causing an automated cleaning process, providing a notification to a device, or both, can include sounding an audible alarm, providing audible instructions, alerting a supervisor or security personnel, or a combination of these. The actions can include restricting a person's access to an area, changing ventilation or other building system settings, logging the incident in a database, or a combination of two or more of these.

In some implementations, the rules can indicate a maximum skin-temperature, whether a person coughs, sneezes, has labored breathing, has a pulse or blood oxygen level that satisfies a threshold, or a combination of two or more of these. For example, the automated cleaning system can apply mask compliance rules differently to people who satisfy a threshold in any of these measures compared to people who do not satisfy a corresponding threshold. For example, when the automated cleaning system detects a person with an elevated skin temperature, e.g., that satisfies the maximum skin-temperature, the automated cleaning system can require the person to wear a facemask to enter a portion of a physical environment while a person without an elevated skin temperature might be exempt from this requirement.

In some implementations, the automated cleaning system can use face recognition or other biometrics, radio-frequency identification or another wireless identification system, or a combination of these, to apply mask compliance rules differently for people who have certain certifications. The certifications can include whether a person has tested immunity, proof of vaccination, or recent negative test for illness, for example. In some examples, the automated cleaning system can use data that indicates articles worn by a person, such as a uniform, badge, certain article of clothing, or a combination of these.

For instance, when the automated cleaning system detects a person who is not wearing a mask in a controlled area, the automated cleaning system can analyze data for the person's face. The automated cleaning system can look up the person's face in a database of tested people, e.g., employees, and determine whether the person tested negative for infectious diseases during a threshold period of time, e.g., in the past two days. Depending on policies for the automated cleaning system, if the person tested negative for infectious diseases within the threshold period of time, the system can determine to not perform any automated cleaning actions based on the person, allow the person to move through one or more portions of a physical environment unmasked, or both.

In some implementations, an automated cleaning device can increase a surface temperature of an area of the device to at least a critical temperature. The critical temperature can be selected to have at least a threshold likelihood of decontaminating any potential pathogens on the automated cleaning device, or a portion of the automated cleaning device. The automated cleaning device can be manufactured from a specially designed plastic or another material that can absorb and dissipate heat quickly. The material can be a film on the surface of one or more buttons included in the device. The film can be thin, so very little energy is needed to achieve the critical temperature.

The surface film can be either heated directly by an electric current or by metallic heating coils embedded in or just below the film. The device can use a short pulse of electric current to heat the film past the critical temperature, to likely decontaminate any pathogens on the surface of the device. The device can then allow the film to dissipate the heat to avoid discomfort to people who might subsequently touch the buttons.

In some implementations, an automated cleaning device can use audio cues, visual cues, or both, to warn bystanders of an active self-sanitization cycle, when the device is safe to touch again, or both. In some examples, the heat/cool cycle can be less than a threshold period of time such that the total energy transfer to a human who touches the device during a self-sanitization cycle will be insufficient to cause harm. This can occur when the surface film has a thickness that is less than a threshold thickness, e.g., is thin enough. In some implementations, the surface film can incorporate capacitive sensing, such that it could sense when a person was touching it, and thus could sense that it had been touched, wait a short period after it was no longer being touch, and activate, deactivating if it sensed touch again.

An automated cleaning device can have any appropriate trigger, detected by the automated cleaning device, the automated cleaning system, or both. For instance, a self-sanitization process for an automated cleaning device can be triggered upon detection of a button press on the device, according to a daily schedule, detection of movement, e.g., of a person walking by the device, detection of a presence within a room that includes the device for a threshold time period, or a combination of two or more of these.

The device can be an AC powered device. The device can include one or more heating coils, e.g., beneath a surface of the device.

In some implementations, the automated cleaning system can use one or more ultraviolet, e.g., ultraviolet C, lights to decontaminate air in a room. To reduce a risk of using an ultraviolet light in an area in which a person, an animal, or both, are located, the automated cleaning system can use sensor data to determine when, where, and for how long an ultraviolet light can be used. For instance, the automated cleaning system can use images captured by a camera at a physical environment to determine where people, animals, or both are located. The automated cleaning system can then use focused ultraviolet, e.g., ultraviolet C, beams in areas in which no people or animals are located to reduce a risk to people and animals. This can enable the automated cleaning system to decontaminate one or more portions of a physical environment on an as-needed basis without introducing new dangers of ultraviolet exposure.

Some examples of ultraviolet sources for the automated cleaning system include ultraviolet projectors. The automated cleaning system can include one or more ultraviolet projectors positioned around a room. Angles of the projectors can be adjusted dynamically based on the portion of the room that needs to be disinfected, to mitigate safety issues, or both. For instance, if there is a potential safety issue for one projector in a room, the automated cleaning system can maintain that projector in an off position and use a different projector at a different angle to decontaminate a portion of the room.

In some examples, one or more of the projectors can be drone-mounted, e.g., instead of being attached to a wall or another fixture in a room. This can enable the automated cleaning system to instruct a drone with an ultraviolet projector to any portion of a room to decontaminate that portion of the room. For instance, a fixed, e.g., wall mounted, ultraviolet projector might be unable to sufficiently decontaminate a target-spot three feet away from the fixed projector. As a result, the automated cleaning system can determine that the fixed projector will be unable to sufficiently decontaminate the target-spot and provide instructions to a drone mounted projector to cause the drone mounted projector to decontaminate the target spot.

In some implementations, the automated cleaning system can cause multiple projectors to target a portion of a physical environment. For example, when each ultraviolet beam is of relatively low-intensity, the automated cleaning system can cause multiple projectors to direct their corresponding beams to converge at a target-spot to increase a likelihood of decontamination at the target-spot. In some implementations, reduced-intensity beams may intentionally be used to reduce the risk of overexposure to people or animals, particularly in an environment with more rapid/unpredictable movement. For example, reduced-intensity beams may even be safe to be used within a room while people are within the room.

In some implementations, the automated cleaning system can include multiple ultraviolet projectors positioned throughout a room. At least some of the projectors can be enabled to adjust a beam angle, a beam intensity, or both. Using this array of projectors, the automated cleaning system can target a region of air in the room by activating the nearest projector with a clear line-of-site to that spot, at an appropriate level of intensity.

In some examples, the automated cleaning system can perform predictive disinfecting. For instance, as people walk around an area, cameras can capture their movements and algorithms, e.g., implemented by the automated cleaning system, can predict a location where a person has at least a threshold likelihood of moving to next. When the automated cleaning system determines that there are no people already in the predicted location, the automated cleaning system can cause focused ultraviolet beams to "pre-cleanse" that location before the person approaches.

In some examples, the automated cleaning system can perform reactive disinfecting. For example, the automated cleaning system can use cameras to capture images depicting of a person in an area breathing, talking, coughing, etc., and the direction in which the person is facing. When the automated cleaning system detects the person walking away from the area, the automated cleaning system can cause targeted ultraviolet beams to disinfect the area, e.g., in which the person previously exhaled. The automated cleaning system can use infrared cameras to determine the potentially infected area of exhaled breath. The automated cleaning system can use infrared camera data to improve the focus of the ultraviolet beams.

In some examples, the automated cleaning system can perform pre-emptive disinfecting. For instance, the automated cleaning system can cause a projector to project ultraviolet light in a specific shapes to disinfect an area, e.g., while avoiding living creatures. The automated cleaning system can select the shape using the area to disinfect, locations of living creatures in the area, or both. The automated cleaning system can dynamically change the shape using data from one or more cameras, e.g., as living creatures such as people and pets move around the area.

In some implementations, the automated cleaning system can analyze residual light projected beyond an intended target to determine when, where, and for how long, a projector should be enabled. For instance, the automated cleaning system can analyze light reflected from the beam's end-point to determine where residual light goes outside of the beam. The automated cleaning system can use a result of the analysis to ensure that people and pets don't inadvertently get exposed to harmful levels of ultraviolet, e.g., ultraviolet C light.

For example, when the automated cleaning system targets a potentially contaminated spot of air three feet away from an ultraviolet projector, the automated cleaning system we can make sure that the spot gets a sufficient dose of ultraviolet light. However, additional ultraviolet light (at lower intensity) will also be projected five feet away from the projector, after the light passes through the spot of air that that is being disinfected. To avoid exposing people or pets in an area that includes the targeted-spot to harmful light, the automated cleaning system can monitor locations of residual light to ensure that the residual light is at least a threshold distance from any people or pets. In some instances, the automated cleaning system can adjust an intensity of an ultraviolet beam when disinfecting a targeted space to ensure that a person, a pet, or both, in the area that includes the targeted spot do not receive a harmful dose of ultraviolet light.

Similarly, the automated cleaning system can adjust an angle, intensity, or both, of an ultraviolet beam based on other objects in a room, e.g., other than people or pets. For example, when an ultraviolet beam from a projector is targeted at a particular spot in the air but the beam will continue past that spot to hit a couch, the automated cleaning system can determine whether to use ultraviolet light from a different projector, to adjust an intensity of the ultraviolet light, or both. In some examples, the automated cleaning system can determine whether an ultraviolet beam has at least a threshold likelihood of hitting a reflective surface, such as a glass-top table. If so, the automated cleaning system can adjust an angle of the beam, or select a different projector to decontaminate an area.

The automated cleaning system can balance two or more of beam intensity, exposure time, and effectiveness. For instance, ultraviolet light's disinfecting ability can based on a combination of intensity and time. A higher-intensity beam can requires less time to disinfect an area while a lower-intensity beam can require more time.

The automated cleaning system can adjust one or more of beam intensity, exposure time, and effectiveness for a target. In some instances, in order to preserve safety, the automated cleaning system might need to sacrifice effectiveness. For example, the automated cleaning system can detect a target three feet away that would require ten seconds of exposure for 100% effectiveness using the maximum-strength ultraviolet beam available. However, if the automated cleaning system detects one or more people in the room who are moving around the room too frequently to allow for the above described beam, the automated cleaning system might only be able to expose that target to ultraviolet light for five seconds in order to reduce contamination, e.g., and potentially not eliminate the contamination.

In some implementations, the automated cleaning system can adjust one or more properties, e.g., beam intensity, exposure time, or which automated cleaning device is used, to reduce resource usage. For instance, the automated cleaning system can select one or more properties to reduce power consumption, cleaning time, or both.

In some implementations, the automated cleaning system can select properties to reduce a likelihood that one or more objects, in an area around a particular object to be cleaned, are also cleaned with the particular object. The automated cleaning system can use the selected properties to perform targeted cleaning of the particular object. The automated cleaning system can use targeted cleaning to reduce resource usage, to reduce a likelihood of potential damage to the one or more objects by the cleaning process, or both.

In some examples, the automated cleaning system can select one or more properties based on the composition of the particular object to be cleaned, one or more objects in an area around the particular object, a potential contaminant of the particular object, or a combination of two or more of these. For instance, the automated cleaning system can select a cleaning duration, a cleaning area, a cleaning type, or a combination of these, using the one or more properties. This can reduce a likelihood that any of the objects might be damaged; reduce resources used, e.g., energy or cleaning chemicals; or both.

Figure 5:
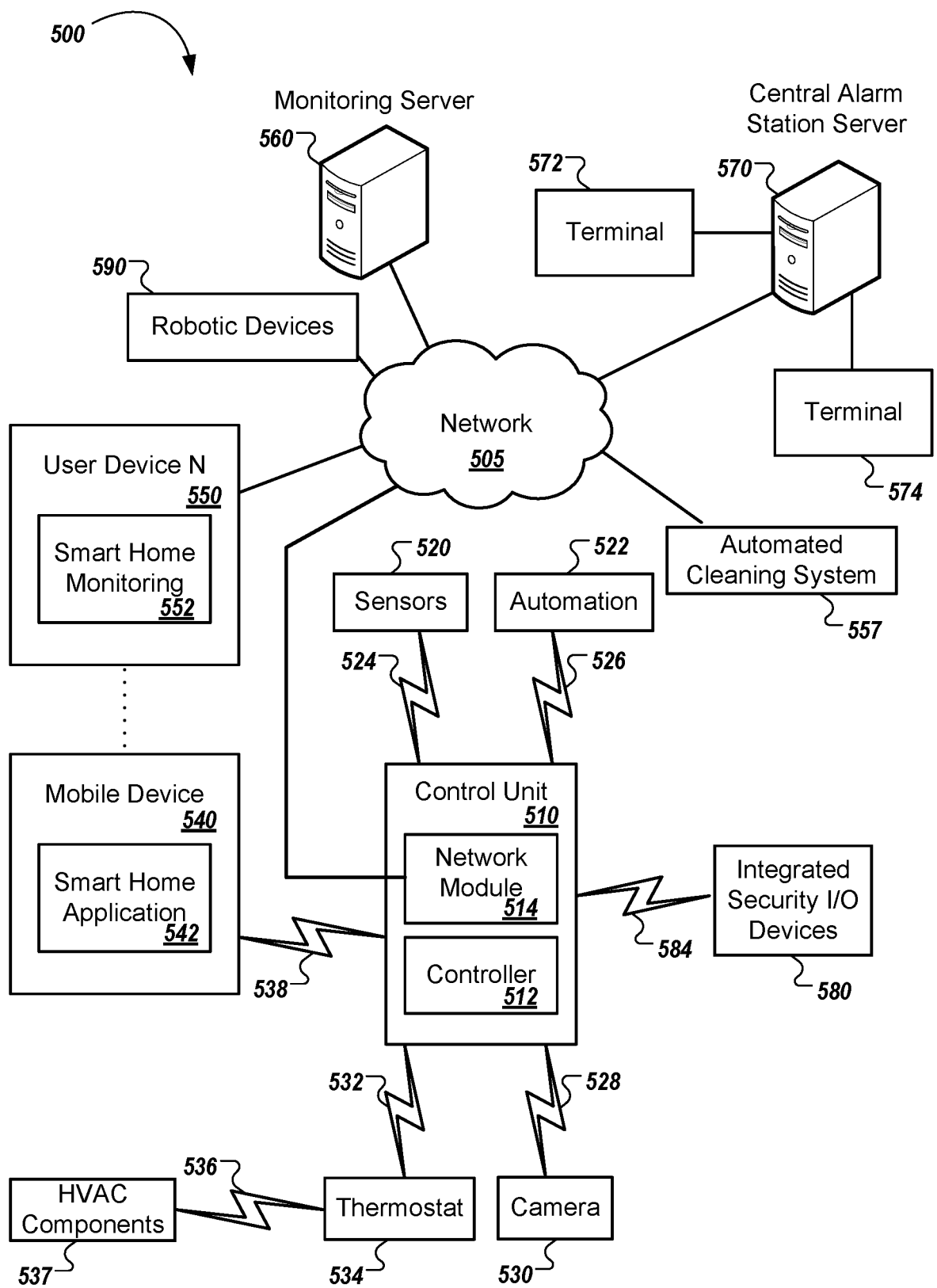
FIG. 5 is a diagram illustrating an example of a home monitoring system.

FIG. 5 is a diagram illustrating an example of a home monitoring system 500. The home monitoring system 500 includes a network 505, a control unit 510, one or more user devices 540 and 550, a monitoring server 560, and a central alarm station server 570. In some examples, the network 505 facilitates communications between the control unit 510, the one or more user devices 540 and 550, the monitoring server 560, and the central alarm station server 570.

The network 505 is configured to enable exchange of electronic communications between devices connected to the network 505. For example, the network 505 may be configured to enable exchange of electronic communications between the control unit 510, the one or more user devices 540 and 550, the monitoring server 560, and the central alarm station server 570. The network 505 may include, for example, one or more of the Internet, Wide Area Networks (WANs), Local Area Networks (LANs), analog or digital wired and wireless telephone networks (e.g., a public switched telephone network (PSTN), Integrated Services Digital Network (ISDN), a cellular network, and Digital Subscriber Line (DSL)), radio, television, cable, satellite, or any other delivery or tunneling mechanism for carrying data. Network 505 may include multiple networks or subnetworks, each of which may include, for example, a wired or wireless data pathway. The network 505 may include a circuit-switched network, a packet-switched data network, or any other network able to carry electronic communications (e.g., data or voice communications). For example, the network 505 may include networks based on the Internet protocol (IP), asynchronous transfer mode (ATM), the PSTN, packet-switched networks based on IP, X.25, or Frame Relay, or other comparable technologies and may support voice using, for example, VoIP, or other comparable protocols used for voice communications. The network 505 may include one or more networks that include wireless data channels and wireless voice channels. The network 505 may be a wireless network, a broadband network, or a combination of networks including a wireless network and a broadband network.

The control unit 510 includes a controller 512 and a network module 514. The controller 512 is configured to control a control unit monitoring system (e.g., a control unit system) that includes the control unit 510. In some examples, the controller 512 may include a processor or other control circuitry configured to execute instructions of a program that controls operation of a control unit system. In these examples, the controller 512 may be configured to receive input from sensors, flow meters, or other devices included in the control unit system and control operations of devices included in the household (e.g., speakers, lights, doors, etc.). For example, the controller 512 may be configured to control operation of the network module 514 included in the control unit 510.

The network module 514 is a communication device configured to exchange communications over the network 505. The network module 514 may be a wireless communication module configured to exchange wireless communications over the network 505. For example, the network module 514 may be a wireless communication device configured to exchange communications over a wireless data channel and a wireless voice channel. In this example, the network module 514 may transmit alarm data over a wireless data channel and establish a two-way voice communication session over a wireless voice channel. The wireless communication device may include one or more of a LTE module, a GSM module, a radio modem, a cellular transmission module, or any type of module configured to exchange communications in one of the following formats: LTE, GSM or GPRS, CDMA, EDGE or EGPRS, EV-DO or EVDO, UMTS, or IP.

The network module 514 also may be a wired communication module configured to exchange communications over the network 505 using a wired connection. For instance, the network module 514 may be a modem, a network interface card, or another type of network interface device. The network module 514 may be an Ethernet network card configured to enable the control unit 510 to communicate over a local area network and/or the Internet. The network module 514 also may be a voice band modem configured to enable the alarm panel to communicate over the telephone lines of Plain Old Telephone Systems (POTS).

The control unit system that includes the control unit 510 includes one or more sensors. For example, the monitoring system 500 may include multiple sensors 520. The sensors 520 may include a lock sensor, a contact sensor, a motion sensor, or any other type of sensor included in a control unit system. The sensors 520 also may include an environmental sensor, such as a temperature sensor, a water sensor, a rain sensor, a wind sensor, a light sensor, a smoke detector, a carbon monoxide detector, an air quality sensor, etc. The sensors 520 further may include a health monitoring sensor, such as a prescription bottle sensor that monitors taking of prescriptions, a blood pressure sensor, a blood sugar sensor, a bed mat configured to sense presence of liquid (e.g., bodily fluids) on the bed mat, etc. In some examples, the health monitoring sensor can be a wearable sensor that attaches to a user in the home. The health monitoring sensor can collect various health data, including pulse, heart-rate, respiration rate, sugar or glucose level, bodily temperature, or motion data. The sensors 520 can also include a radio-frequency identification (RFID) sensor that identifies a particular article that includes a pre-assigned RFID tag.

The control unit 510 communicates with the home automation controls 522 and a camera 530 to perform monitoring. The home automation controls 522 are connected to one or more devices that enable automation of actions in the home. For instance, the home automation controls 522 may be connected to one or more lighting systems and may be configured to control operation of the one or more lighting systems. Also, the home automation controls 522 may be connected to one or more electronic locks at the home and may be configured to control operation of the one or more electronic locks (e.g., control Z-Wave locks using wireless communications in the Z-Wave protocol). Further, the home automation controls 522 may be connected to one or more appliances at the home and may be configured to control operation of the one or more appliances. The home automation controls 522 may include multiple modules that are each specific to the type of device being controlled in an automated manner. The home automation controls 522 may control the one or more devices based on commands received from the control unit 510. For instance, the home automation controls 522 may cause a lighting system to illuminate an area to provide a better image of the area when captured by a camera 530.

The camera 530 may be a video/photographic camera or other type of optical sensing device configured to capture images. For instance, the camera 530 may be configured to capture images of an area within a building or home monitored by the control unit 510. The camera 530 may be configured to capture single, static images of the area or video images of the area in which multiple images of the area are captured at a relatively high frequency (e.g., thirty images per second) or both. The camera 530 may be controlled based on commands received from the control unit 510.

The camera 530 may be triggered by several different types of techniques. For instance, a Passive Infra-Red (PIR) motion sensor may be built into the camera 530 and used to trigger the camera 530 to capture one or more images when motion is detected. The camera 530 also may include a microwave motion sensor built into the camera and used to trigger the camera 530 to capture one or more images when motion is detected. The camera 530 may have a "normally open" or "normally closed" digital input that can trigger capture of one or more images when external sensors (e.g., the sensors 520, PIR, door/window, etc.) detect motion or other events. In some implementations, the camera 530 receives a command to capture an image when external devices detect motion or another potential alarm event. The camera 530 may receive the command from the controller 512 or directly from one of the sensors 520.

In some examples, the camera 530 triggers integrated or external illuminators (e.g., Infra-Red, Z-wave controlled "white" lights, lights controlled by the home automation controls 522, etc.) to improve image quality when the scene is dark. An integrated or separate light sensor may be used to determine if illumination is desired and may result in increased image quality.

The camera 530 may be programmed with any combination of time/day schedules, system "arming state", or other variables to determine whether images should be captured or not when triggers occur. The camera 530 may enter a low-power mode when not capturing images. In this case, the camera 530 may wake periodically to check for inbound messages from the controller 512. The camera 530 may be powered by internal, replaceable batteries, e.g., if located remotely from the control unit 510. The camera 530 may employ a small solar cell to recharge the battery when light is available. The camera 530 may be powered by the controller's 512 power supply if the camera 530 is co-located with the controller 512.

In some implementations, the camera 530 communicates directly with the monitoring server 560 over the Internet. In these implementations, image data captured by the camera 530 does not pass through the control unit 510 and the camera 530 receives commands related to operation from the monitoring server 560.

The system 500 also includes thermostat 534 to perform dynamic environmental control at the home. The thermostat 534 is configured to monitor temperature and/or energy consumption of an HVAC system associated with the thermostat 534, and is further configured to provide control of environmental (e.g., temperature) settings. In some implementations, the thermostat 534 can additionally or alternatively receive data relating to activity at a home and/or environmental data at a home, e.g., at various locations indoors and outdoors at the home. The thermostat 534 can directly measure energy consumption of the HVAC system associated with the thermostat, or can estimate energy consumption of the HVAC system associated with the thermostat 534, for example, based on detected usage of one or more components of the HVAC system associated with the thermostat 534. The thermostat 534 can communicate temperature and/or energy monitoring information to or from the control unit 510 and can control the environmental (e.g., temperature) settings based on commands received from the control unit 510.

In some implementations, the thermostat 534 is a dynamically programmable thermostat and can be integrated with the control unit 510. For example, the dynamically programmable thermostat 534 can include the control unit 510, e.g., as an internal component to the dynamically programmable thermostat 534. In addition, the control unit 510 can be a gateway device that communicates with the dynamically programmable thermostat 534. In some implementations, the thermostat 534 is controlled via one or more home automation controls 522.

A module 537 is connected to one or more components of an HVAC system associated with a home, and is configured to control operation of the one or more components of the HVAC system. In some implementations, the module 537 is also configured to monitor energy consumption of the HVAC system components, for example, by directly measuring the energy consumption of the HVAC system components or by estimating the energy usage of the one or more HVAC system components based on detecting usage of components of the HVAC system. The module 537 can communicate energy monitoring information and the state of the HVAC system components to the thermostat 534 and can control the one or more components of the HVAC system based on commands received from the thermostat 534.

The system 500 includes automated cleaning system 557. The automated cleaning system 557 can be computing devices (e.g., a computer, microcontroller, FPGA, ASIC, or other device capable of electronic computation) capable of receiving data related to the automated cleaning system and communicating electronically with the monitoring system control unit 510.

In some examples, the system 500 further includes one or more robotic devices 590. The robotic devices 590 may be any type of robots that are capable of moving and taking actions that assist in home monitoring. For example, the robotic devices 590 may include drones that are capable of moving throughout a home based on automated control technology and/or user input control provided by a user. In this example, the drones may be able to fly, roll, walk, or otherwise move about the home. The drones may include helicopter type devices (e.g., quad copters), rolling helicopter type devices (e.g., roller copter devices that can fly and also roll along the ground, walls, or ceiling) and land vehicle type devices (e.g., automated cars that drive around a home). In some cases, the robotic devices 590 may be robotic devices 590 that are intended for other purposes and merely associated with the system 500 for use in appropriate circumstances. For instance, a robotic vacuum cleaner device may be associated with the monitoring system 500 as one of the robotic devices 590 and may be controlled to take action responsive to monitoring system events.

In some examples, the robotic devices 590 automatically navigate within a home. In these examples, the robotic devices 590 include sensors and control processors that guide movement of the robotic devices 590 within the home. For instance, the robotic devices 590 may navigate within the home using one or more cameras, one or more proximity sensors, one or more gyroscopes, one or more accelerometers, one or more magnetometers, a global positioning system (GPS) unit, an altimeter, one or more sonar or laser sensors, and/or any other types of sensors that aid in navigation about a space. The robotic devices 590 may include control processors that process output from the various sensors and control the robotic devices 590 to move along a path that reaches the desired destination and avoids obstacles. In this regard, the control processors detect walls or other obstacles in the home and guide movement of the robotic devices 590 in a manner that avoids the walls and other obstacles.

In addition, the robotic devices 590 may store data that describes attributes of the home. For instance, the robotic devices 590 may store a floorplan and/or a three-dimensional model of the home that enables the robotic devices 590 to navigate the home. During initial configuration, the robotic devices 590 may receive the data describing attributes of the home, determine a frame of reference to the data (e.g., a home or reference location in the home), and navigate the home based on the frame of reference and the data describing attributes of the home. Further, initial configuration of the robotic devices 590 also may include learning of one or more navigation patterns in which a user provides input to control the robotic devices 590 to perform a specific navigation action (e.g., fly to an upstairs bedroom and spin around while capturing video and then return to a home charging base). In this regard, the robotic devices 590 may learn and store the navigation patterns such that the robotic devices 590 may automatically repeat the specific navigation actions upon a later request.

In some examples, the robotic devices 590 may include data capture and recording devices. In these examples, the robotic devices 590 may include one or more cameras, one or more motion sensors, one or more microphones, one or more biometric data collection tools, one or more temperature sensors, one or more humidity sensors, one or more air flow sensors, and/or any other types of sensor that may be useful in capturing monitoring data related to the home and users in the home. The one or more biometric data collection tools may be configured to collect biometric samples of a person in the home with or without contact of the person. For instance, the biometric data collection tools may include a fingerprint scanner, a hair sample collection tool, a skin cell collection tool, and/or any other tool that allows the robotic devices 590 to take and store a biometric sample that can be used to identify the person (e.g., a biometric sample with DNA that can be used for DNA testing).

In some implementations, the robotic devices 590 may include output devices. In these implementations, the robotic devices 590 may include one or more displays, one or more speakers, and/or any type of output devices that allow the robotic devices 590 to communicate information to a nearby user.

The robotic devices 590 also may include a communication module that enables the robotic devices 590 to communicate with the control unit 510, each other, and/or other devices. The communication module may be a wireless communication module that allows the robotic devices 590 to communicate wirelessly. For instance, the communication module may be a Wi-Fi module that enables the robotic devices 590 to communicate over a local wireless network at the home. The communication module further may be a 900 MHz wireless communication module that enables the robotic devices 590 to communicate directly with the control unit 510. Other types of short-range wireless communication protocols, such as Bluetooth, Bluetooth LE, Z-wave, Zig-Bee, etc., may be used to allow the robotic devices 590 to communicate with other devices in the home. In some implementations, the robotic devices 590 may communicate with each other or with other devices of the system 500 through the network 505.

The robotic devices 590 further may include processor and storage capabilities. The robotic devices 590 may include any suitable processing devices that enable the robotic devices 590 to operate applications and perform the actions described throughout this disclosure. In addition, the robotic devices 590 may include solid-state electronic storage that enables the robotic devices 590 to store applications, configuration data, collected sensor data, and/or any other type of information available to the robotic devices 590.

The robotic devices 590 are associated with one or more charging stations. The charging stations may be located at predefined home base or reference locations in the home. The robotic devices 590 may be configured to navigate to the charging stations after completion of tasks needed to be performed for the home monitoring system 500. For instance, after completion of a monitoring operation or upon instruction by the control unit 510, the robotic devices 590 may be configured to automatically fly to and land on one of the charging stations. In this regard, the robotic devices 590 may automatically maintain a fully charged battery in a state in which the robotic devices 590 are ready for use by the home monitoring system 500.

The charging stations may be contact based charging stations and/or wireless charging stations. For contact based charging stations, the robotic devices 590 may have readily accessible points of contact that the robotic devices 590 are capable of positioning and mating with a corresponding contact on the charging station. For instance, a helicopter type robotic device may have an electronic contact on a portion of its landing gear that rests on and mates with an electronic pad of a charging station when the helicopter type robotic device lands on the charging station. The electronic contact on the robotic device may include a cover that opens to expose the electronic contact when the robotic device is charging and closes to cover and insulate the electronic contact when the robotic device is in operation.

For wireless charging stations, the robotic devices 590 may charge through a wireless exchange of power. In these cases, the robotic devices 590 need only locate themselves closely enough to the wireless charging stations for the wireless exchange of power to occur. In this regard, the positioning needed to land at a predefined home base or reference location in the home may be less precise than with a contact based charging station. Based on the robotic devices 590 landing at a wireless charging station, the wireless charging station outputs a wireless signal that the robotic devices 590 receive and convert to a power signal that charges a battery maintained on the robotic devices 590.

In some implementations, each of the robotic devices 590 has a corresponding and assigned charging station such that the number of robotic devices 590 equals the number of charging stations. In these implementations, the robotic devices 590 always navigate to the specific charging station assigned to that robotic device. For instance, a first robotic device may always use a first charging station and a second robotic device may always use a second charging station.

In some examples, the robotic devices 590 may share charging stations. For instance, the robotic devices 590 may use one or more community charging stations that are capable of charging multiple robotic devices 590. The community charging station may be configured to charge multiple robotic devices 590 in parallel. The community charging station may be configured to charge multiple robotic devices 590 in serial such that the multiple robotic devices 590 take turns charging and, when fully charged, return to a predefined home base or reference location in the home that is not associated with a charger. The number of community charging stations may be less than the number of robotic devices 590.

Also, the charging stations may not be assigned to specific robotic devices 590 and may be capable of charging any of the robotic devices 590. In this regard, the robotic devices 590 may use any suitable, unoccupied charging station when not in use. For instance, when one of the robotic devices 590 has completed an operation or is in need of battery charge, the control unit 510 references a stored table of the occupancy status of each charging station and instructs the robotic device to navigate to the nearest charging station that is unoccupied.

The system 500 further includes one or more integrated security devices 580. The one or more integrated security devices may include any type of device used to provide alerts based on received sensor data. For instance, the one or more control units 510 may provide one or more alerts to the one or more integrated security input/output devices 580. Additionally, the one or more control units 510 may receive sensor data from the sensors 520 and determine whether to provide an alert to the one or more integrated security input/output devices 580.

The sensors 520, the home automation controls 522, the camera 530, the thermostat 534, and the integrated security devices 580 may communicate with the controller 512 over communication links 524, 526, 528, 532, 538, and 584. The communication links 524, 526, 528, 532, 538, and 584 may be a wired or wireless data pathway configured to transmit signals from the sensors 520, the home automation controls 522, the camera 530, the thermostat 534, and the integrated security devices 580 to the controller 512. The sensors 520, the home automation controls 522, the camera 530, the thermostat 534, and the integrated security devices 580 may continuously transmit sensed values to the controller 512, periodically transmit sensed values to the controller 512, or transmit sensed values to the controller 512 in response to a change in a sensed value.

The communication links 524, 526, 528, 532, 538, and 584 may include a local network. The sensors 520, the home automation controls 522, the camera 530, the thermostat 534, and the integrated security devices 580, and the controller 512 may exchange data and commands over the local network. The local network may include 802.11 "Wi-Fi" wireless Ethernet (e.g., using low-power Wi-Fi chipsets), Z-Wave, ZigBee, Bluetooth, "Homeplug" or other "Powerline" networks that operate over AC wiring, and a Category 5 (CAT5) or Category 6 (CAT6) wired Ethernet network. The local network may be a mesh network constructed based on the devices connected to the mesh network.

The monitoring server 560 is an electronic device configured to provide monitoring services by exchanging electronic communications with the control unit 510, the one or more user devices 540 and 550, and the central alarm station server 570 over the network 505. For example, the monitoring server 560 may be configured to monitor events (e.g., alarm events) generated by the control unit 510. In this example, the monitoring server 560 may exchange electronic communications with the network module 514 included in the control unit 510 to receive information regarding events (e.g., alerts) detected by the control unit 510. The monitoring server 560 also may receive information regarding events (e.g., alerts) from the one or more user devices 540 and 550.

In some examples, the monitoring server 560 may route alert data received from the network module 514 or the one or more user devices 540 and 550 to the central alarm station server 570. For example, the monitoring server 560 may transmit the alert data to the central alarm station server 570 over the network 505.

The monitoring server 560 may store sensor and image data received from the monitoring system 500 and perform analysis of sensor and image data received from the monitoring system 500. Based on the analysis, the monitoring server 560 may communicate with and control aspects of the control unit 510 or the one or more user devices 540 and 550.

The monitoring server 560 may provide various monitoring services to the system 500. For example, the monitoring server 560 may analyze the sensor, image, and other data to determine an activity pattern of a resident of the home monitored by the system 500. In some implementations, the monitoring server 560 may analyze the data for alarm conditions or may determine and perform actions at the home by issuing commands to one or more of the controls 522, possibly through the control unit 510.

The central alarm station server 570 is an electronic device configured to provide alarm monitoring service by exchanging communications with the control unit 510, the one or more mobile devices 540 and 550, and the monitoring server 560 over the network 505. For example, the central alarm station server 570 may be configured to monitor alerting events generated by the control unit 510. In this example, the central alarm station server 570 may exchange communications with the network module 514 included in the control unit 510 to receive information regarding alerting events detected by the control unit 510. The central alarm station server 570 also may receive information regarding alerting events from the one or more mobile devices 540 and 550 and/or the monitoring server 560.

The central alarm station server 570 is connected to multiple terminals 572 and 574. The terminals 572 and 574 may be used by operators to process alerting events. For example, the central alarm station server 570 may route alerting data to the terminals 572 and 574 to enable an operator to process the alerting data. The terminals 572 and 574 may include general-purpose computers (e.g., desktop personal computers, workstations, or laptop computers) that are configured to receive alerting data from a server in the central alarm station server 570 and render a display of information based on the alerting data. For instance, the controller 512 may control the network module 514 to transmit, to the central alarm station server 570, alerting data indicating that a sensor 520 detected motion from a motion sensor via the sensors 520. The central alarm station server 570 may receive the alerting data and route the alerting data to the terminal 572 for processing by an operator associated with the terminal 572. The terminal 572 may render a display to the operator that includes information associated with the alerting event (e.g., the lock sensor data, the motion sensor data, the contact sensor data, etc.) and the operator may handle the alerting event based on the displayed information.

In some implementations, the terminals 572 and 574 may be mobile devices or devices designed for a specific function. Although FIG. 5 illustrates two terminals for brevity, actual implementations may include more (and, perhaps, many more) terminals.

The one or more authorized user devices 540 and 550 are devices that host and display user interfaces. For instance, the user device 540 is a mobile device that hosts or runs one or more native applications (e.g., the smart home application 542). The user device 540 may be a cellular phone or a non-cellular locally networked device with a display. The user device 540 may include a cell phone, a smart phone, a tablet PC, a personal digital assistant ("PDA"), or any other portable device configured to communicate over a network and display information. For example, implementations may also include Blackberry-type devices (e.g., as provided by Research in Motion), electronic organizers, iPhone-type devices (e.g., as provided by Apple), iPod devices (e.g., as provided by Apple) or other portable music players, other communication devices, and handheld or portable electronic devices for gaming, communications, and/or data organization. The user device 540 may perform functions unrelated to the monitoring system, such as placing personal telephone calls, playing music, playing video, displaying pictures, browsing the Internet, maintaining an electronic calendar, etc.

The user device 540 includes a smart home application 542. The smart home application 542 refers to a software/firmware program running on the corresponding mobile device that enables the user interface and features described throughout. The user device 540 may load or install the smart home application 542 based on data received over a network or data received from local media. The smart home application 542 runs on mobile devices platforms, such as iPhone, iPod touch, Blackberry, Google Android, Windows Mobile, etc. The smart home application 542 enables the user device 540 to receive and process image and sensor data from the monitoring system.

The user device 550 may be a general-purpose computer (e.g., a desktop personal computer, a workstation, or a laptop computer) that is configured to communicate with the monitoring server 560 and/or the control unit 510 over the network 505. The user device 550 may be configured to display a smart home user interface 552 that is generated by the user device 550 or generated by the monitoring server 560. For example, the user device 550 may be configured to display a user interface (e.g., a web page) provided by the monitoring server 560 that enables a user to perceive images captured by the camera 530 and/or reports related to the monitoring system. Although FIG. 5 illustrates two user devices for brevity, actual implementations may include more (and, perhaps, many more) or fewer user devices.

In some implementations, the one or more user devices 540 and 550 communicate with and receive monitoring system data from the control unit 510 using the communication link 538. For instance, the one or more user devices 540 and 550 may communicate with the control unit 510 using various local wireless protocols such as Wi-Fi, Bluetooth, Z-wave, ZigBee, HomePlug (Ethernet over power line), or wired protocols such as Ethernet and USB, to connect the one or more user devices 540 and 550 to local security and automation equipment. The one or more user devices 540 and 550 may connect locally to the monitoring system and its sensors and other devices. The local connection may improve the speed of status and control communications because communicating through the network 505 with a remote server (e.g., the monitoring server 560) may be significantly slower.

Although the one or more user devices 540 and 550 are shown as communicating with the control unit 510, the one or more user devices 540 and 550 may communicate directly with the sensors and other devices controlled by the control unit 510. In some implementations, the one or more user devices 540 and 550 replace the control unit 510 and perform the functions of the control unit 510 for local monitoring and long range/offsite communication.

In other implementations, the one or more user devices 540 and 550 receive monitoring system data captured by the control unit 510 through the network 505. The one or more user devices 540, 550 may receive the data from the control unit 510 through the network 505 or the monitoring server 560 may relay data received from the control unit 510 to the one or more user devices 540 and 550 through the network 505. In this regard, the monitoring server 560 may facilitate communication between the one or more user devices 540 and 550 and the monitoring system.

In some implementations, the one or more user devices 540 and 550 may be configured to switch whether the one or more user devices 540 and 550 communicate with the control unit 510 directly (e.g., through link 538) or through the monitoring server 560 (e.g., through network 505) based on a location of the one or more user devices 540 and 550. For instance, when the one or more user devices 540 and 550 are located close to the control unit 510 and in range to communicate directly with the control unit 510, the one or more user devices 540 and 550 use direct communication. When the one or more user devices 540 and 550 are located far from the control unit 510 and not in range to communicate directly with the control unit 510, the one or more user devices 540 and 550 use communication through the monitoring server 560.

Although the one or more user devices 540 and 550 are shown as being connected to the network 505, in some implementations, the one or more user devices 540 and 550 are not connected to the network 505. In these implementations, the one or more user devices 540 and 550 communicate directly with one or more of the monitoring system components and no network (e.g., Internet) connection or reliance on remote servers is needed.

In some implementations, the one or more user devices 540 and 550 are used in conjunction with only local sensors and/or local devices in a house. In these implementations, the system 500 includes the one or more user devices 540 and 550, the sensors 520, the home automation controls 522, the camera 530, the robotic devices 590, and the automated cleaning system 557. The one or more user devices 540 and 550 receive data directly from the sensors 520, the home automation controls 522, the camera 530, the robotic devices 590, and the automated cleaning system 557 and sends data directly to the sensors 520, the home automation controls 522, the camera 530, the robotic devices 590, and the automated cleaning system 557. The one or more user devices 540, 550 provide the appropriate interfaces/processing to provide visual surveillance and reporting.

In other implementations, the system 500 further includes network 505 and the sensors 520, the home automation controls 522, the camera 530, the thermostat 534, the robotic devices 590, and the automated cleaning system 557 are configured to communicate sensor and image data to the one or more user devices 540 and 550 over network 505 (e.g., the Internet, cellular network, etc.). In yet another implementation, the sensors 520, the home automation controls 522, the camera 530, the thermostat 534, the robotic devices 590, and the automated cleaning system 557 (or a component, such as a bridge/router) are intelligent enough to change the communication pathway from a direct local pathway when the one or more user devices 540 and 550 are in close physical proximity to the sensors 520, the home automation controls 522, the camera 530, the thermostat 534, the robotic devices 590, and the automated cleaning system 557 to a pathway over network 505 when the one or more user devices 540 and 550 are farther from the sensors 520, the home automation controls 522, the camera 530, the thermostat 534, the robotic devices 590, and the automated cleaning system 557. In some examples, the system leverages GPS information from the one or more user devices 540 and 550 to determine whether the one or more user devices 540 and 550 are close enough to the sensors 520, the home automation controls 522, the camera 530, the thermostat 534, the robotic devices 590, and the automated cleaning system 557 to use the direct local pathway or whether the one or more user devices 540 and 550 are far enough from the sensors 520, the home automation controls 522, the camera 530, the thermostat 534, the robotic devices 590, and the automated cleaning system 557 that the pathway over network 505 is required. In other examples, the system leverages status communications (e.g., pinging) between the one or more user devices 540 and 550 and the sensors 520, the home automation controls 522, the camera 530, the thermostat 534, the robotic devices 590, and the automated cleaning system 557 to determine whether communication using the direct local pathway is possible. If communication using the direct local pathway is possible, the one or more user devices 540 and 550 communicate with the sensors 520, the home automation controls 522, the camera 530, the thermostat 534, the robotic devices 590, and the automated cleaning system 557 using the direct local pathway. If communication using the direct local pathway is not possible, the one or more user devices 540 and 550 communicate with the sensors 520, the home automation controls 522, the camera 530, the thermostat 534, the robotic devices 590, and the automated cleaning system 557 using the pathway over network 505.

In some implementations, the system 500 provides end users with access to images captured by the camera 530 to aid in decision-making. The system 500 may transmit the images captured by the camera 530 over a wireless WAN network to the user devices 540 and 550. Because transmission over a wireless WAN network may be relatively expensive, the system 500 can use several techniques to reduce costs while providing access to significant levels of useful visual information (e.g., compressing data, down-sampling data, sending data only over inexpensive LAN connections, or other techniques).

In some implementations, a state of the monitoring system 500 and other events sensed by the monitoring system 500 may be used to enable/disable video/image recording devices (e.g., the camera 530). In these implementations, the camera 530 may be set to capture images on a periodic basis when the alarm system is armed in an "away" state, but set not to capture images when the alarm system is armed in a "home" state or disarmed. In addition, the camera 530 may be triggered to begin capturing images when the alarm system detects an event, such as an alarm event, a door-opening event for a door that leads to an area within a field of view of the camera 530, or motion in the area within the field of view of the camera 530. In other implementations, the camera 530 may capture images continuously, but the captured images may be stored or transmitted over a network when needed.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially designed ASICs (application-specific integrated circuits).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

The invention claimed is:

1. A computer-implemented method comprising:
   detecting, by an automated cleaning system, movement within a physical environment;
   determining, by the automated cleaning system and using data that represents the movement, that one or more threshold criteria for cleaning at least a portion of the physical environment are satisfied, wherein determining that the one or more threshold criteria are satisfied comprises:
   determining, by the automated cleaning system and using data that represents the movement, that there is at least a threshold likelihood that a person will move to a physical area that includes the portion of the physical environment; and
   determining, by the automated cleaning system, that there is not likely another person in the physical area that includes the portion of the physical environment; and
   in response to determining that the one or more threshold criteria for cleaning at least the portion of the physical environment are satisfied including i) determining that there is at least the threshold likelihood that the person will move to the physical area that includes the portion of the physical environment and ii) determining that there is not likely another person in the physical area that includes the portion of the physical environment, sending, by the automated cleaning system, an instruction to a device in the physical environment to cause the device to initiate a cleaning process of at least the portion of the physical environment that will likely finish before the person will likely move to the physical area that includes the portion of the physical environment.

2. The method of claim 1, comprising:
   after sending the instruction to the device, determining that a threshold likelihood of decontaminating at least the portion of the physical environment is satisfied; and
   in response to determining that the threshold likelihood of decontaminating at least the portion of the physical environment is satisfied, sending a second instruction to the device to cause the device to halt the cleaning process.

3. The method of claim 1, wherein sending the instruction comprises sending, by the automated cleaning system, the instruction to the device a) that is located in the portion of the physical environment, b) to cause the device to initiate the cleaning process, and c) to present a message that indicates when the device is safe to touch again.

4. The method of claim 1, comprising:
   determining, by the automated cleaning system, a type of cleaning required for at least the portion of the physical environment; and
   selecting, from a group of multiple devices that each can clean respective portions of the physical environment, the device using the type of cleaning required,
   wherein sending the instruction to the device in the physical environment to cause the device to initiate the cleaning process of at least the portion of the physical environment is responsive to selecting the device using the type of cleaning required.

5. The method of claim 1, comprising:
   determining, by the automated cleaning system, one or more properties for the portion of the physical environment; and
   determining, using the one or more properties for the portion of the physical environment, one or more settings for the device, wherein:
   sending the instruction to the device comprises sending, by the automated cleaning system, the instruction to the device in the physical environment to cause the device to initiate a cleaning process of at least the portion of the physical environment using the one or more settings.

6. The method of claim 1, comprising:
   determining, by the automated cleaning system and using data for the portion of the physical environment, a minimum area for the portion of the physical environment to be cleaned given the one or more threshold criteria for cleaning at least the portion of the physical environment that are satisfied, wherein:
sending the instruction to the device comprises sending, by the automated cleaning system, the instruction to the device in the physical environment to increase a likelihood that the device will clean the minimum area for the portion of the physical environment without cleaning an area surrounding the portion of the physical environment.

7. The method of claim 6, wherein sending the instruction comprises sending, by the automated cleaning system, the instruction to the device in the physical environment to cause the device to initiate a cleaning process of only the minimum area for the portion of the physical environment.

8. The method of claim 1, comprising:
selecting, from multiple cleaning processes and using data that indicates that there is at least the threshold likelihood that the person will move to the physical area, the cleaning process that would not be selected if there was not the indication that there is at least the threshold likelihood that the person will move to the physical area,
wherein sending the instruction comprises sending, to the device, the instruction to initiate the cleaning process a) that will likely finish before the person will likely move to the physical area that includes portion of the physical environment, and b) that would not be selected if there was not the indication that there is at least the threshold likelihood that the person will move to the physical area.

9. The method of claim 1, comprising:
selecting, from multiple cleaning processes and using data for the person who will likely move to the physical area that includes the portion of the physical environment, a particular cleaning process,
wherein sending the instruction comprises sending, to the device, the instruction to initiate the particular cleaning process for the person who will likely move to the physical area that includes the portion of the physical environment.

10. A non-transitory computer storage medium encoded with instructions that, when executed by one or more computers, cause the one or more computers to perform operations comprising:
detecting, by an automated cleaning system that comprises the one or more computers, movement within a physical environment;
determining, by the automated cleaning system and using data that represents the movement, that one or more threshold criteria for cleaning at least a portion of the physical environment are satisfied, wherein determining that the one or more threshold criteria are satisfied comprises:
determining, by the automated cleaning system and using data that represents the movement, that there is at least a threshold likelihood that a person will move to a physical area that includes the portion of the physical environment; and
determining, by the automated cleaning system, that there is not likely another person in the physical area that includes the portion of the physical environment; and
in response to determining that the one or more threshold criteria for cleaning at least the portion of the physical environment are satisfied including i) determining that there is at least the threshold likelihood that the person will move to the physical area that includes the portion of the physical environment and ii) determining that there is not likely another person in the physical area that includes the portion of the physical environment, sending, by the automated cleaning system, an instruction to a device in the physical environment to cause the device to initiate a cleaning process of at least the portion of the physical environment that will likely finish before the person will likely move to the physical area that includes portion of the physical environment.

11. The non-transitory computer storage medium of claim 10, the operations comprising:
after sending the instruction to the device, determining that a threshold likelihood of decontaminating at least the portion of the physical environment is satisfied; and
in response to determining that the threshold likelihood of decontaminating at least the portion of the physical environment is satisfied, sending a second instruction to the device to cause the device to halt the cleaning process.

12. The non-transitory computer storage medium of claim 10, wherein sending the instruction comprises sending, by the automated cleaning system, the instruction to the device a) that is located in the portion of the physical environment, b) to cause the device to initiate the cleaning process, and c) to present a message that indicates when the device is safe to touch again.

13. The non-transitory computer storage medium of claim 10, the operations comprising:
determining, by the automated cleaning system, a type of cleaning required for at least the portion of the physical environment; and
selecting, from a group of multiple devices that each can clean respective portions of the physical environment, the device using the type of cleaning required,
wherein sending the instruction to the device in the physical environment to cause the device to initiate the cleaning process of at least the portion of the physical environment is responsive to selecting the device using the type of cleaning required.

14. The non-transitory computer storage medium of claim 10, the operations comprising:
determining, by the automated cleaning system, one or more properties for the portion of the physical environment; and
determining, using the one or more properties for the portion of the physical environment, one or more settings for the device, wherein:
sending the instruction to the device comprises sending, by the automated cleaning system, the instruction to the device in the physical environment to cause the device to initiate a cleaning process of at least the portion of the physical environment using the one or more settings.

15. The non-transitory computer storage medium of claim 10, the operations comprising:
determining, by the automated cleaning system and using data for the portion of the physical environment, a minimum area for the portion of the physical environment to be cleaned given the one or more threshold criteria for cleaning at least the portion of the physical environment that are satisfied, wherein:
sending the instruction to the device comprises sending, by the automated cleaning system, the instruction to the device in the physical environment to increase a likelihood that the device will clean the minimum area for the portion of the physical environment without cleaning an area surrounding the portion of the physical environment.

16. The non-transitory computer storage medium of claim 15, wherein sending the instruction comprises sending, by the automated cleaning system, the instruction to the device in the physical environment to cause the device to initiate a cleaning process of only the minimum area for the portion of the physical environment.

17. A system comprising one or more computers and one or more storage devices on which are stored instructions that are operable, when executed by the one or more computers, to cause the one or more computers to perform operations comprising:
- detecting, by an automated cleaning system that comprises the one or more computers, movement within a physical environment;
- determining, by the automated cleaning system and using data that represents the movement, that one or more threshold criteria for cleaning at least a portion of the physical environment are satisfied, wherein determining that the one or more threshold criteria are satisfied comprises:
  - determining, by the automated cleaning system and using data that represents the movement, that there is at least a threshold likelihood that a person will move to a physical area that includes the portion of the physical environment; and
  - determining, by the automated cleaning system, that there is not likely another person in the physical area that includes the portion of the physical environment; and
- in response to determining that the one or more threshold criteria for cleaning at least the portion of the physical environment are satisfied including i) determining that there is at least the threshold likelihood that the person will move to the physical area that includes the portion of the physical environment and ii) determining that there is not likely another person in the physical area that includes the portion of the physical environment:
  - determining a cleaning process for at least the portion of the physical environment and that will likely finish before the person will likely move to the physical area that includes the portion of the physical environment; and
  - sending, by the automated cleaning system, an instruction to a device in the physical environment to cause the device to initiate the cleaning process of at least the portion of the physical environment that will likely finish before the person will likely move to the physical area that includes the portion of the physical environment.

18. The system of claim 17, the operations comprising:
after sending the instruction to the device, determining that a threshold likelihood of decontaminating at least the portion of the physical environment is satisfied; and
in response to determining that the threshold likelihood of decontaminating at least the portion of the physical environment is satisfied, sending a second instruction to the device to cause the device to halt the cleaning process.

19. The system of claim 17, wherein sending the instruction comprises sending, by the automated cleaning system, the instruction to the device a) that is located in the portion of the physical environment, b) to cause the device to initiate the cleaning process, and c) to present a message that indicates when the device is safe to touch again.

20. The system of claim 17, the operations comprising:
determining, by the automated cleaning system, a type of cleaning required for at least the portion of the physical environment; and
selecting, from a group of multiple devices that each can clean respective portions of the physical environment, the device using the type of cleaning required,
wherein sending the instruction to the device in the physical environment to cause the device to initiate the cleaning process of at least the portion of the physical environment is responsive to selecting the device using the type of cleaning required.

* * * * *